(12) United States Patent
Cuello et al.

(10) Patent No.: US 10,604,732 B2
(45) Date of Patent: Mar. 31, 2020

(54) ACCORDION AIR LOOP BIOREACTOR

(71) Applicants: Arizona Board of Regents on Behalf of the University of Arizona, Tucson, AZ (US); Biopharmia AS, Oslo (NO)

(72) Inventors: Joel L. Cuello, Tucson, AZ (US); Cody Brown, Tucson, AZ (US); Roald A. Flo, Oslo (NO); Takanori Hoshino, Tucson, AZ (US); Sara S. Kuwahara, Tucson, AZ (US)

(73) Assignees: Arizona Board of Regents on Behalf of the University of Arizona, Tucson, AZ (US); Biopharmia AS, Oslo (NO)

( * ) Notice: Subject to any disclaimer, the term of this patent is extended or adjusted under 35 U.S.C. 154(b) by 155 days.

(21) Appl. No.: 15/531,334

(22) PCT Filed: Nov. 25, 2015

(86) PCT No.: PCT/US2015/062738
§ 371 (c)(1),
(2) Date: May 26, 2017

(87) PCT Pub. No.: WO2016/086165
PCT Pub. Date: Jun. 2, 2016

(65) Prior Publication Data
US 2017/0355946 A1  Dec. 14, 2017

Related U.S. Application Data

(60) Provisional application No. 62/085,455, filed on Nov. 28, 2014.

(51) Int. Cl.
*C12M 1/00* (2006.01)
*C12M 1/12* (2006.01)

(52) U.S. Cl.
CPC ............ *C12M 29/08* (2013.01); *C12M 21/02* (2013.01); *C12M 25/14* (2013.01)

(58) Field of Classification Search
CPC ...... C12M 41/00; C12M 29/04; C12M 37/00; C12M 23/48; C12M 23/42; C12M 29/10; C12M 29/06; C12M 25/14; C12M 25/16; C12M 27/00; C12M 21/02; C12M 21/08; C12M 23/14; C12M 23/28; C12M 27/04; C12M 27/06; C12M 27/16; C12M 33/14; C12M 23/04; C12M 23/22; C12M 23/26; C12M 23/34; C12M 23/46; C12M 23/56; C12M 25/18; C12M 27/02; C12M 27/10; C12M 27/20; C12M 29/08; C12M 29/20; C12M 31/00; C12M 31/02; C12M 31/10; C12M 33/00; C12M 35/02; C12M 41/10; C12M 41/12; C12M 41/26; C12M 41/44; C12M 41/48; C12M 47/02; C12M 23/38; C12M 25/02; C12M 27/18; C12M 29/00; C12M 37/02; C12M 41/40; C12M 41/46; C12M 23/12; C12M 23/16; Y10S 435/809; A61K 35/28; A61K 2300/00; A61K 35/407; A61K 35/50; A61K 35/32; A61K 35/35; A61K 35/36; A61K 2035/124; A61K 35/12; A61K 2035/122; C12N 5/0075; C12N 2510/02; C12N 2513/00; C12N 2527/00; C12N 2531/00; C12N 1/00; C12N 2500/62; C12N 2501/119; C12N 2501/12; C12N 2501/155; C12N 2501/16; C12N 2501/237; C12N 2501/39; C12N 2501/415; C12N 2501/602; C12N 2501/603; C12N 2501/604; C12N 2501/606; C12N 2506/1384; C12N 2506/45; C12N 2510/00; C12N 2533/90; C12N 5/0605; C12N 5/067; C12N 5/0696; C12N 2509/10; C12N 2533/30; C12N 5/00; C12N 5/0062; C12N 5/0602; C12N 5/0604; C12N 5/0652; C12N 5/0667; C12N 5/0668; C12N 5/0671; C12N 5/0663; C12N 5/0653; C12N 5/0669; C12N 2500/84; C12N 5/0018; C12N 2537/10; C12N 5/0068; C12N 5/0657; C12N 5/069; Y10T 137/0318; B01J 19/0093; B01J 2219/00783; B01J 2219/00833; B01J 2219/0084; B01J 2219/0086; B01J 2219/00907; B01L 2300/161;
(Continued)

(56) References Cited

U.S. PATENT DOCUMENTS

2006/0024822 A1  2/2006  Chang et al.
2011/0287541 A1  11/2011 Cuello et al.
2012/0028234 A1  2/2012  Guertin et al.

FOREIGN PATENT DOCUMENTS

WO  WO 2015/116963 A1  8/2015

*Primary Examiner* — Deborah K Ware
(74) *Attorney, Agent, or Firm* — Klarquist Sparkman, LLP

(57) ABSTRACT

Disclosed herein are bioreactors that include a vessel with sides and a bottom, at least one opening in the vessel connected to a means for introducing a gas, and at least one scaffold in the vessel oriented substantially vertically in the vessel. The scaffolds are two substantially parallel sheets that are separated by a distance ($d_{min}$). Also disclosed herein are bioreactors that include a vessel with sides and a bottom, at least one opening in the vessel connected to a means for introducing a gas, and at least two scaffolds in the vessel oriented substantially vertically in the vessel. The disclosure also includes methods of culturing cells including incubating a suspension of cells in a disclosed bioreactor and introducing a gas through the at least one opening in the vessel. In some examples, the cells include microalgae, macroalgae, bacteria, fungi, insect cells, plant cells, or animal cells.

16 Claims, 19 Drawing Sheets

(58) Field of Classification Search
CPC ..... B01L 3/502707; B32B 37/18; C07K 1/16; G01N 33/54393; G01N 33/5061; G01N 33/502; G01N 33/5082; A61L 27/3895; A61L 27/2823; A61L 27/3886; A61L 1/0247; A61L 27/18; A61L 27/14; A61L 2400/06; A61L 2430/20; A61L 27/3826; A61L 27/3834; A61L 27/50; A61L 27/56; A61P 37/06; B33Y 10/00; B33Y 30/00; B33Y 70/00; C08L 75/04; C08L 67/02; B29C 48/05; B29C 48/92; D01D 5/0076; D01D 5/0092; A61B 2560/0223; A61B 5/0002; A61B 5/14532; A61B 5/14546; A61B 5/14865; A61B 5/1495; A61B 5/6833; A61B 5/6848; A61B 5/6849; A61B 5/726; A61B 5/743; A61F 2/2472; C08G 63/52; C08J 2367/00; C08J 3/243; C08J 3/246; C08J 3/28

See application file for complete search history.

FIG. 1A
FIG. 1B
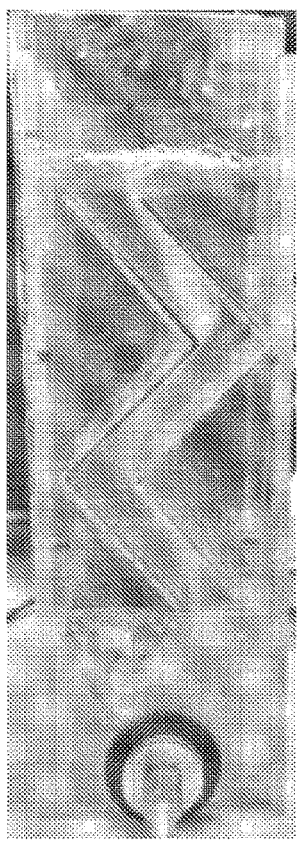
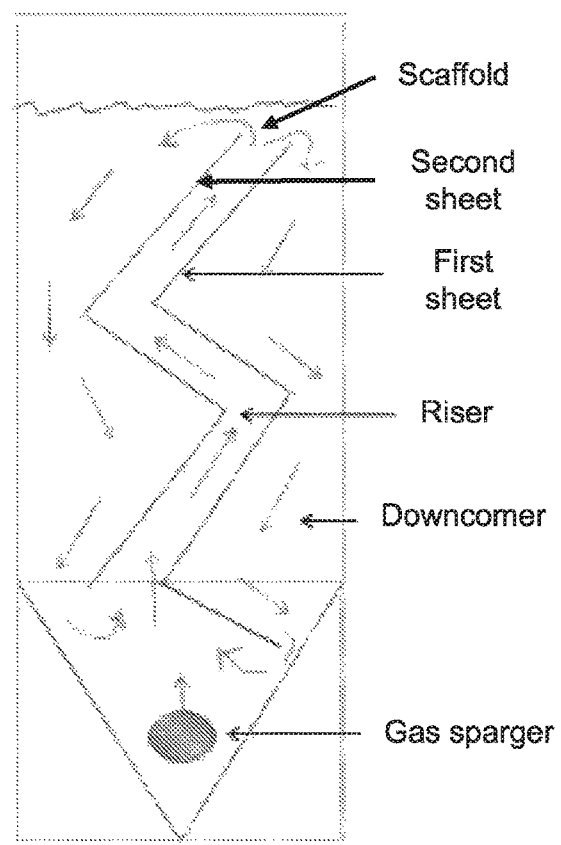

FIG. 2A
FIG. 2B
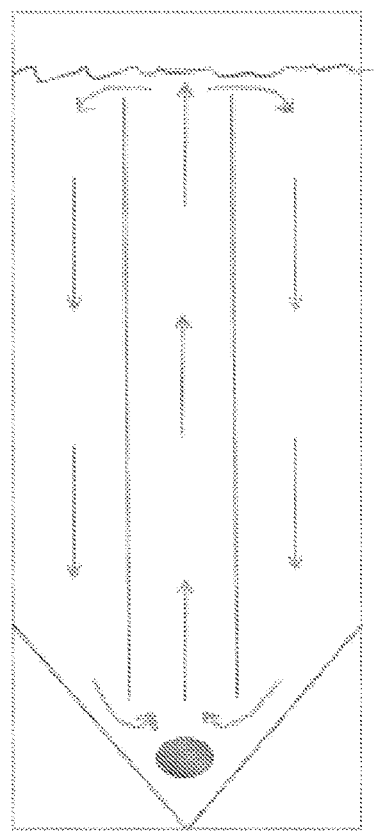
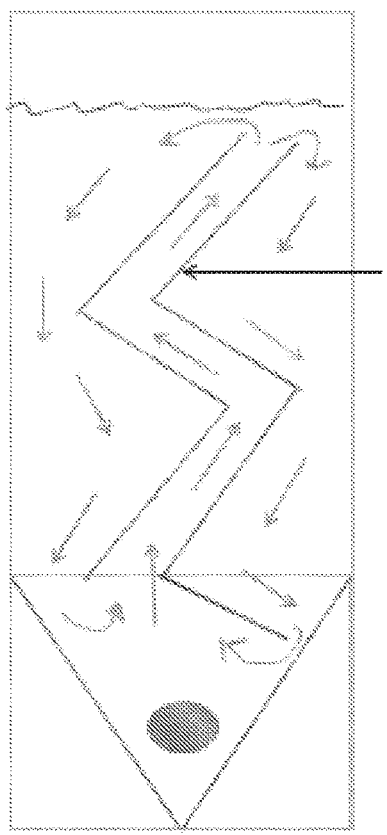
Accordion scaffold $\Theta = s/r$

FIG. 6A
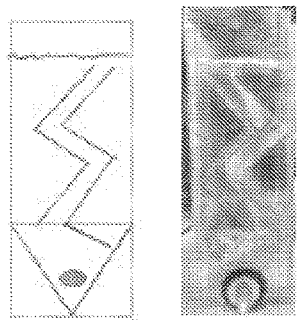
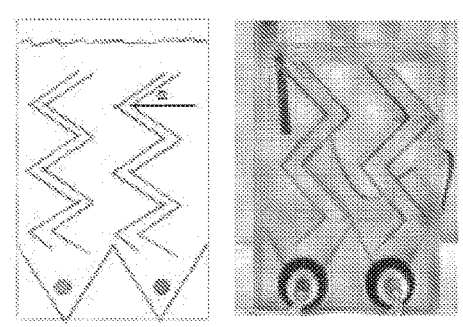
FIG. 6B
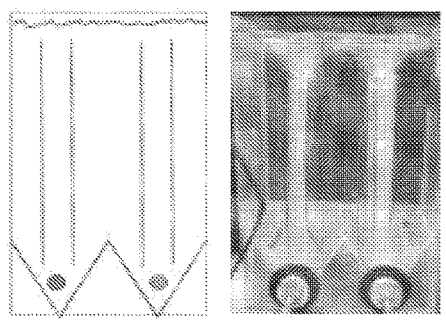
FIG. 6C
FIG. 6D
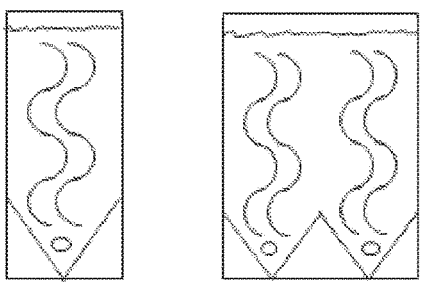
FIG. 6E
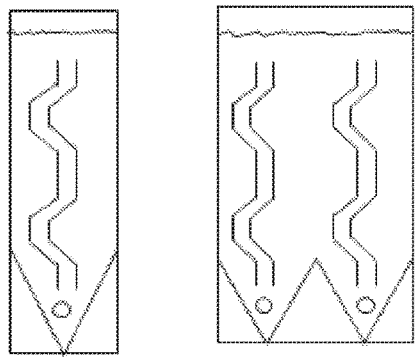

FIG. 7A
FIG. 7B
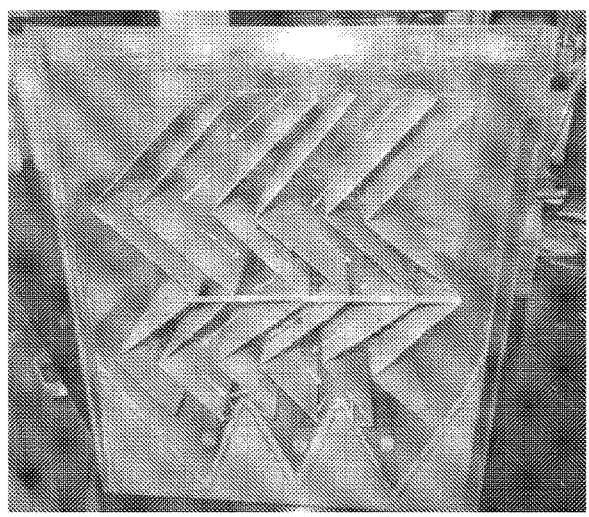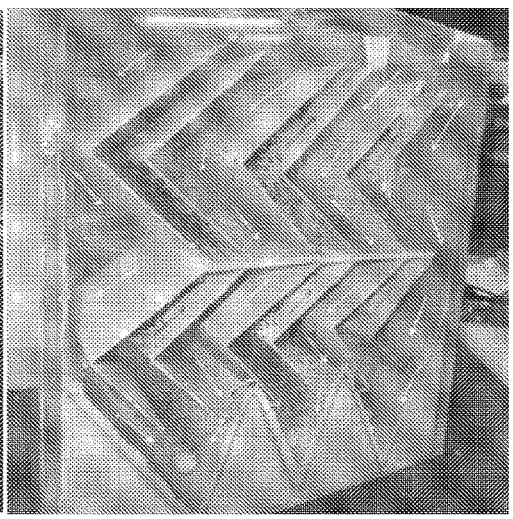
FIG. 7C
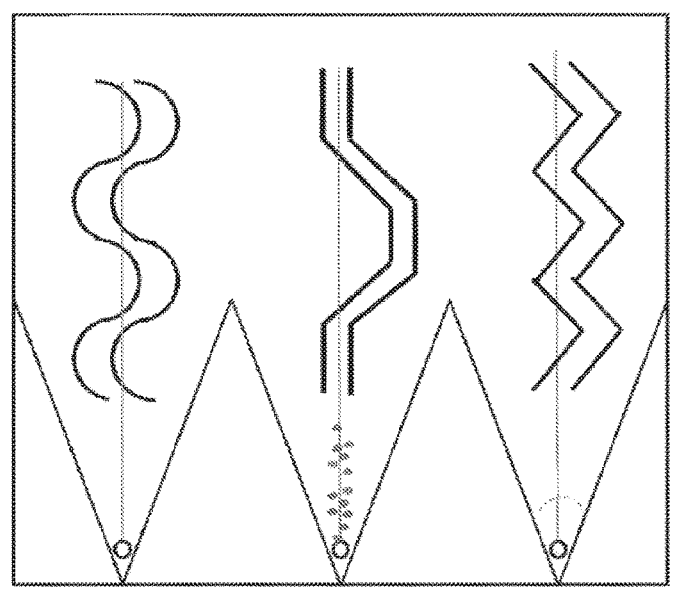

ACCORDION AIR LOOP BIOREACTOR

CROSS REFERENCE TO RELATED APPLICATION

This is the § 371 National Stage of International Application No. PCT/US2015/062738, filed Nov. 25, 2015, which was published in English under PCT Article 21(2), which in turn claims the benefit of U.S. Provisional Patent Application No. 62/085,455, filed Nov. 28, 2014, which is incorporated herein by reference in its entirety.

FIELD

This disclosure relates to bioreactors and methods of their use, for example for cell culture.

BACKGROUND

The photoautotrophic growth of microorganisms or cells is enabled by the photosynthetic capacity of the chlorophyll-containing microorganisms or cells, whereby carbon dioxide ($CO_2$), through photosynthetic carbon fixation, serves as the carbon (or food) source. Photoautotrophic growth requires the presence of light for photosynthesis to occur. A steady supply of $CO_2$ when light is available also promotes culture growth.

By contrast, heterotrophic growth takes place when the microorganisms or cells, in the absence of photosynthetic $CO_2$ fixation, rely on exogenous carbon-based molecules, typically sugars such as glucose or sucrose, present in the liquid culture medium as their carbon (or food) source. Heterotrophic growth necessitates a sterile or axenic growth environment to avoid culture contamination; otherwise, unwanted and competing bacteria and other microorganisms would grow in the culture owing to the presence of the carbon-based food source. This mode of growth also requires a steady supply of oxygen ($O_2$) which the microorganisms or cells need as they breakdown the carbon-based molecules through the process of respiration. Since light is not essential, heterotrophic production is generally carried out in darkness. Mixotrophic growth takes place when the microorganisms or cells grow both photoautotrophically and heterotrophically.

Commercial large-scale production of microalgae began in the late 1960s in Japan then spread throughout the world in the 1970s and 1980s. In recent years the number of commercial large-scale facilities around the world has increased at nearly exponential rate as demand for animal feed, nutraceuticals, vitamins and lipids, biofuels and bioplastics has increased. As natural resources become increasingly scarce it is evident that the need for large-scale commercial production of microalgae and other cell types will also grow.

SUMMARY

Disclosed herein in several embodiments is a pneumatic or "airlift"-type bioreactor (referred to herein in some embodiments as an "Accordion Air Loop" bioreactor). The disclosed bioreactors can be used for photoautotrophic, mixotrophic, or heterotrophic growth and production of microalgae and other microorganisms (such as bacteria or fungi), as well as plant, animal, and insect cells. As described herein, the disclosed bioreactors provide advantageous properties, including in some examples low-shear culture environment, improved liquid mixing, and/or improved gas mass transfer efficiency.

Disclosed herein are bioreactors that include a vessel with sides and a bottom, at least one opening in the vessel connected to a means for introducing a gas, and at least one scaffold in the vessel oriented substantially vertically in the vessel. The scaffolds included in the disclosed bioreactors comprise at least two substantially parallel sheets (a first sheet and a second sheet) that are separated by a distance ($d_{min}$). In some embodiments, the first and second sheets are substantially parallel and include portions or sections at least some of which are oriented at an angle different from 0° relative to the horizontal axis of the vessel, such that the scaffold configuration suggests an accordion. In some embodiments, the first and second sheets are substantially parallel and include portions or sections oriented at alternating angles (also referred to herein as a "zigzag" configuration). In other embodiments, the first and second sheets are substantially parallel and include portions or sections that are oriented at an angle or are substantially vertical (e.g., substantially parallel to the sides of the vessel), for example in an alternating pattern (also referred to herein as a "mixed" angular and straight scaffold configuration). In still further embodiments, the first and second sheets are substantially parallel and are oriented in a series of two or more curved or bent sections (also referred to herein as a "curved" scaffold configuration).

Also disclosed herein are bioreactors that include a vessel with sides and a bottom, at least one opening in the vessel connected to a means for introducing a gas, and at least two scaffolds in the vessel oriented substantially vertically in the vessel. The at least two scaffolds may have one or more of a zigzag, mixed, or curved configuration as discussed above, or may have substantially vertical first and second sheets.

The disclosure also includes methods of culturing cells including incubating a suspension of cells in a disclosed bioreactor. In some examples, the cells include microalgae, macroalgae, bacteria, fungi, insect cells, plant cells, or animal cells (such as mammalian cells). The methods include photoautotrophic, heterotrophic, or mixotrophic cell culture.

The foregoing and other features of the disclosure will become more apparent from the following detailed description, which proceeds with reference to the accompanying figures.

BRIEF DESCRIPTION OF THE DRAWINGS

FIGS. 1A and 1B are a digital image (FIG. 1A) and a schematic drawing (FIG. 1B) of an exemplary embodiment of an Accordion Air Loop bioreactor.

FIGS. 2A and 2B are schematics showing a conventional airlift bioreactor (FIG. 2A) and an exemplary zig-zag configuration of an Accordion Air Loop bioreactor (FIG. 2B). Arrows show direction of liquid flow.

FIG. 5D shows the angle of curvature θ of the curved scaffold as a function of the arc length s and the radius r.

FIGS. 6A-6E are a series of schematics (left) and digital images (right) showing exemplary Accordion Air Loop bioreactors with one (FIG. 6A) or two accordion scaffolds (FIGS. 6B and 6C). FIG. 6D is a pair of schematics showing exemplary configurations with one (left) or two (right) curved scaffolds. FIG. 6E is a pair of schematics showing exemplary configurations with one (left) or two (right) mixed angled-vertical scaffolds.

FIGS. 7A and 7B are a pair of digital images showing an Accordion Air Loop bioreactor with three scaffolds. Dark arrows show riser and light arrows show downcomer. FIG. 7C is a schematic drawing showing an exemplary Accordion Air Loop bioreactor including scaffolds of three different types.

FIG. 16A illustrates an embodiment without the arm or bridge. FIGS. 16B-16D include horizontal arms or bridges at the top and/or bottom of the bioreactor between the sparger and the scaffold.

FIG. 17A) or low gas flow rate (0.1 vvm; FIG. 17B) for two Accordion air loop bioreactor configurations and corresponding air lift bioreactor controls. Error bars are standard deviation with n=4.

FIG. 18A) or low gas flow rate (0.1 vvm; FIG. 18B) for two Accordion air loop bioreactor configurations and corresponding air lift bioreactor controls. Error bars are standard deviation with n=2. Open circles are single airlift configuration; closed circles are single airloop accordion configuration; open diamonds are double airlift configuration; and closed diamonds are double airloop accordion configuration.

DETAILED DESCRIPTION

Figure 3:
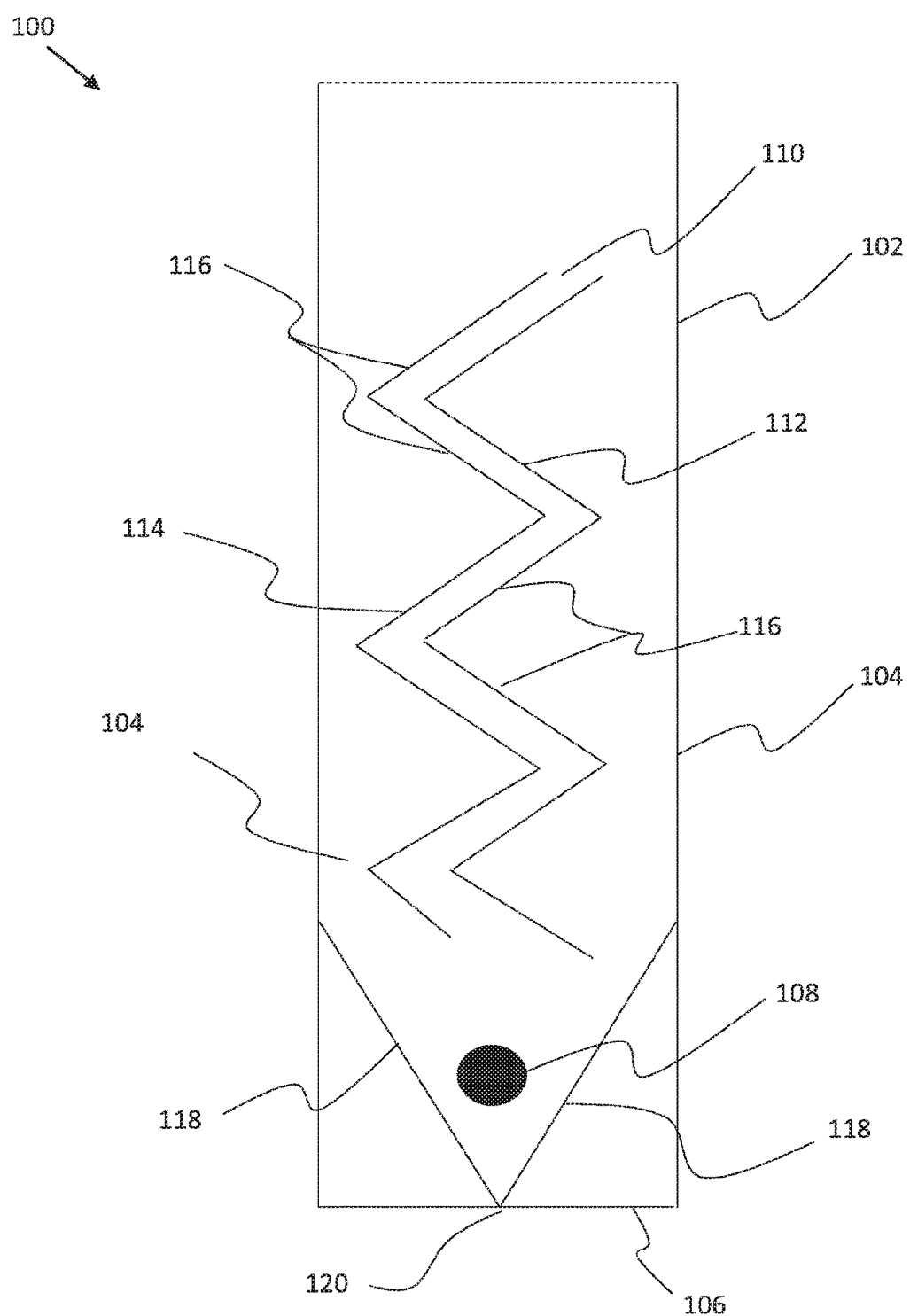
FIG. 3 illustrates an exemplary embodiment of an air-loop accordion bioreactor.

The airlift-type bioreactors disclosed herein provide for cell culture or biomass production with advantageous properties including in some examples low-shear culture environment, improved liquid mixing, and/or improved gas mass transfer efficiency, for example compared to conventional airlift bioreactors. The disclosed bioreactors have a low-shear culture environment compared with stirred-tank bioreactors which make use of a fast-rotating impeller. Furthermore, compared with air-sparged flat-panel bioreactors, the disclosed bioreactors have robustly defined (or non-random) liquid circulation patterns, meeting a significant requirement for successful scale up.

Although bioreactors and methods are described herein primarily with respect to algae culture (for example, the culture of microalgae), the disclosed bioreactors and methods in their several embodiments are also suitable for culture of other photosynthetic cells, including for example, cyanobacteria. In other examples, the bioreactors and methods are also suitable for culture of other cells and/or organisms, such as fungi, bacteria, insect cells, plant cells or plant tissue, and mammalian cells or tissue.

Unless otherwise explained, all technical and scientific terms used herein have the same meaning as commonly understood by one of ordinary skill in the art to which this disclosure belongs. The singular terms "a," "an," and "the" include plural referents unless the context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety for all purposes. In case of conflict, the present specification, including explanations of terms, will control. In addition, the materials, methods, and examples are illustrative only and not intended to be limiting.

I. Overview of Several Embodiments

Disclosed herein are bioreactors that include a vessel having sides and a bottom (and optionally a top), at least one opening in the vessel connected to a means for introducing a gas (for example for introducing a gas into a liquid in the vessel), and at least one scaffold inside the vessel. The scaffold provides a riser structure (for upward flow of liquid and gas bubbles) in some embodiments or a downcomer structure (for downward flow of liquid) in other embodiments (e.g., FIGS. 1B, 15A, and 16B). The scaffold is constructed from two sheets (for example flexible, semi-rigid, or rigid material) substantially parallel to one another that are placed in the vessel in a substantially vertical orientation. In some embodiments, at least a portion of the scaffold rests on the bottom of the vessel (see, e.g., FIG. 7A), in such a way that the downcomer flow can circulate toward the sparger and be redirected upward. In other embodiments, the scaffold is fastened to the sides of the vessel, for example directly attached to one or more sides of the vessel or attached to pegs, strips, or other structures that are themselves attached to one or more sides of the vessel. In one non-limiting example, FIGS. 7A and 7B illustrate attachment of a scaffold structure in the vessel by connecting to a strip of metal attached to the side of the vessel. In other examples, a combination of attachment to one or more sides of the vessel and having at least a portion of the scaffold resting on the bottom of the vessel.

As used herein, the term "substantially parallel" indicates that two objects (such as a first sheet and a second sheet) are largely, but not necessarily wholly or perfectly parallel to one another. Similarly, the terms "substantially vertical" and "substantially horizontal" indicate that two objects are largely, but not necessarily wholly or perfectly vertical or horizontal to one another, respectively. In some non-limiting examples, the term "substantially" includes a variance of less than 20% (for example, less than 15%, 10%, 5%, 4%, 3%, 2%, or 1%) from being perfectly parallel, vertical, or horizontal.

The scaffold is a structure that creates a space (e.g., the space between the two substantially parallel sheets) that is the riser or downcomer, depending on the particular bioreactor embodiment. In some embodiments, the space between the two substantially parallel sheets (referred to herein as $d_{min}$) is determined relative to the total width (W) of the vessel (e.g., as a ratio of $d_{min}/W$). In some non-limiting examples, $d_{min}/W$ is about 0.05-0.33 (such as about 0.1-0.25).

In some embodiments, the two sheets (e.g., a first sheet and a second sheet) are made of sections, at least some of which are oriented at an angle different from 0° relative to the horizontal axis of the vessel. In some embodiments, the substantially parallel first and second sheets include portions or sections that are oriented at alternating angles (also referred to herein as a "zigzag" configuration). In other embodiments, the substantially parallel first and second sheets include portions or sections that are oriented at an angle or are substantially vertical (e.g., substantially parallel to the sides of the vessel), for example in an alternating pattern (also referred to herein as a "mixed" angular and straight scaffold configuration). In some examples, the angle ("pitch angle") between sections of the scaffold is about 10° to 80° relative to the horizontal axis of the vessel (such as about 20° to 60° or about 30° to 50°, for example, about 10°, 15°, 20°, 25°, 30°, 35°, 40°, 45°, 50°, 55°, 60°, 65°, 70°, 75°, or 80°). In particular examples, the pitch angle is about 30° or about 45°. In other examples, the angle between sections of the scaffold is greater than 90° relative to the horizontal axis of the vessel (such as about 95-160°, for example, about 100°, 110°, 120°, 130°, 140°, 150°, or 160°). In still further embodiments, the parallel first and second sheets are oriented in a series of two or more curved or bent sections (also referred to herein as a "curved" scaffold configuration). The angle of curvature is the central angle which the are of curvature subtends (e.g., FIG. 5D). In some examples, the angle of curvature between sections of the scaffold is about 20° to 170° (such as about 40° to 160° or about 60° to 120°, for example about 20°, 30°, 40°, 50°, 60°, 70°, 80°, 90°, 100°, 110°, 120°, 130°, 140°, 150°, 160° or 180°). In particular examples, the angle of curvature is about 80° or about 160°.

In other embodiments of the disclosure, the bioreactor includes a vessel having sides and a bottom (and optionally a top), at least one opening in the vessel connected to a means for introducing a gas (for example for introducing a gas into a liquid in the vessel), and at least two scaffolds (such as 2, 3, 4, 5, 10, 15, or more scaffolds) in the vessel. The two or more scaffolds can include zigzag, mixed straight and angular, and/or curved configurations as discussed above. In other embodiments, the two or more scaffolds are each made up of two substantially vertical sheets (e.g., FIG. 6C). In embodiments including two or more scaffolds, the scaffolds may be of the same type (e.g., two or more zigzag scaffolds, two or more mixed straight and angular scaffolds, two or more curved scaffolds, or two or more substantially vertical scaffolds) or may be different (e.g., a combination of zigzag, mixed straight and angular, curved, and or vertical scaffolds). One example of an embodiment including different scaffolds types is shown schematically in FIG. 7C.

Figure 8:
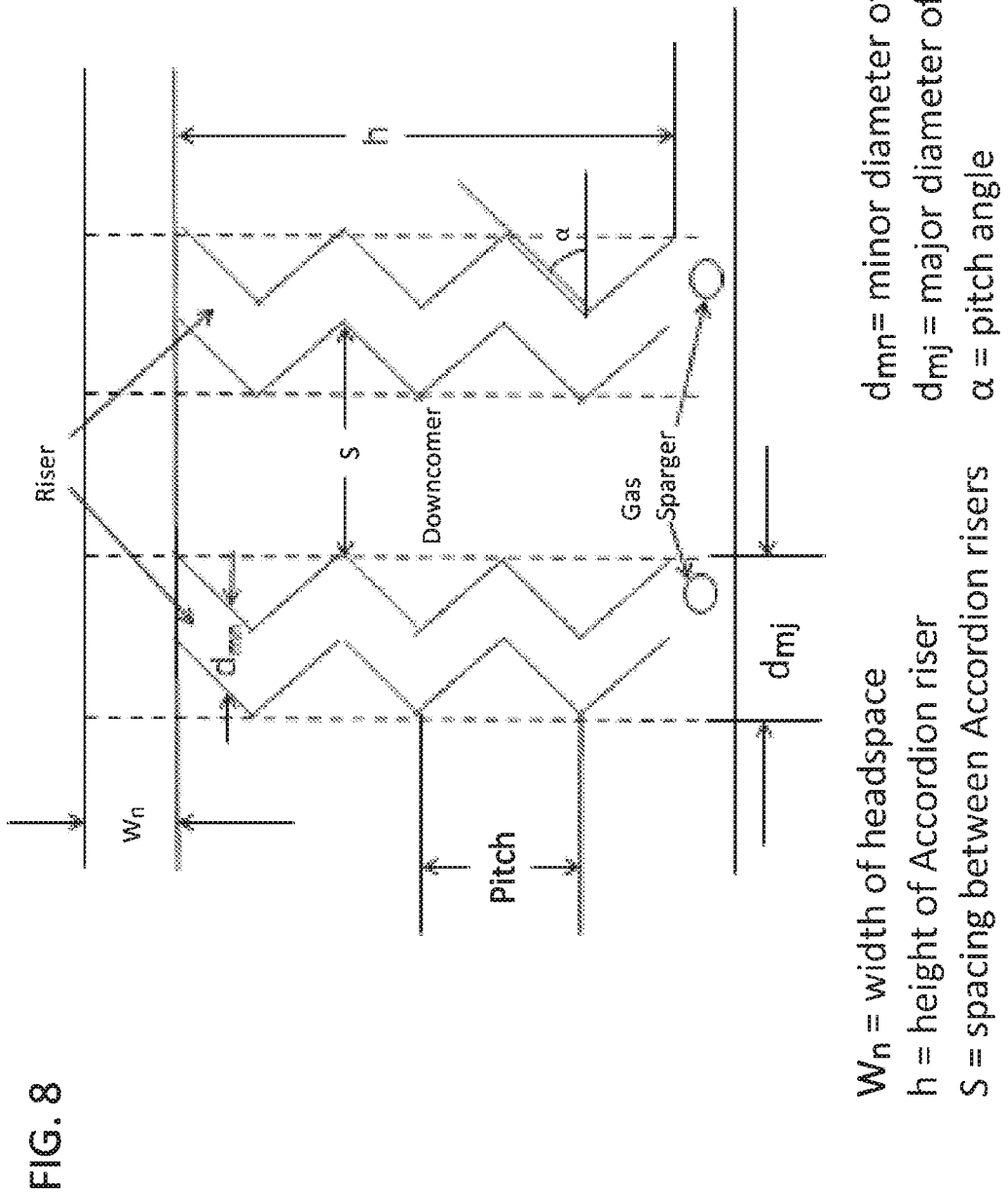
FIG. 8 is an illustration of dimensions and nomenclature used for the Accordion Air Loop bioreactors, shown with respect to a zigzag scaffold configuration.

In embodiments with two or more scaffolds in a vessel, the scaffolds are placed in the vessel with space between them that serves as a downcomer space (e.g. FIG. 8). In some examples, the spacing between the scaffolds is about 2 to 8 inches (such as about 3 to 6 inches). In particular examples, the distance between the scaffolds is about 4 inches. In other examples, the spacing or distance between the scaffolds (s) is determined relative to the width of the vessel (W) in the form of the ratio s/W. In some non-limiting examples, s/W is about 0.10 to 0.45 (such as about 0.125-0.438 or about 0.15-0.4). In embodiments with two or more scaffolds, the vessel may include two or more openings for introduction of gas, for example, one opening for each scaffold in the vessel.

In some examples, the scaffold (e.g., the first sheet and the second sheet) is made of a rigid material, such as glass, polycarbonate, polyvinyl chloride, or metal. In other examples, the scaffold is made of a flexible material, such as a flexible plastic (such as flexible polyethylene, polyvinyl chloride, polypropylene, polyurethane, high density polyethylene, or polyacrylate). The scaffold (e.g., the first sheet and the second sheet) is generally formed from a continuous (solid) material, but in some embodiments may include one or more openings or perforations. In some examples, the material is capable of withstanding high heat (for example, steam), in order to allow sterilization of the scaffold. Thus, in one example, the scaffold is made from stainless steel. In some examples, the sections of the scaffold are formed by bending or molding a continuous sheet of material to produce a scaffold with sections oriented at selected angles. In other examples, the sections of the scaffold are formed by fastening together pieces of the material, for example with adhesive (such as a waterproof adhesive, for example waterproof silicone or epoxy) or a solvent, such as methyl ethyl ketone.

The vessel is a container including sides and a bottom. In some embodiments, the sides are straight or substantially straight. Thus, in some examples, the vessel has four substantially straight sides and is a square or rectangular container. However, the vessel can have any desired shape, including triangular, trapezoidal, or having five or more sides. In other embodiments, the sides of the vessel are curved. Thus, in some examples, the vessel is cylindrical. One of skill in the art can select a suitable shape for the vessel used herein, so long as it can accommodate one or more scaffolds. In some examples, the vessel additionally includes a top (such as a removable lid), for example, if a closed or substantially closed system is desired.

The vessel can be made of any material capable of accommodating the one or more scaffolds and holding liquid. In some examples, the vessel is made of a rigid material, such as glass, polycarbonate, polyvinyl chloride, or metal (for example, stainless steel). In some embodiments, at least a portion (or all) of the vessel is made from transparent or semi-transparent material (for example, for use in photoautotrophic culture methods). In other embodiments, at least a portion (or all) of the vessel is made from opaque material (for example, for use in heterotrophic culture methods).

One of skill in the art can select a size for the vessel, for example depending on the desired volume. In some examples, the volume of the vessel is about 1 liter to about 10,000 liters (such as about 1-10 liters, about 2-25 liters, about 5-50 liters, about 10-100 liters, about 50-5000 liters, about 100-2000 liters, or about 2500-5000 liters). In particular examples, the volume of the vessel is about 2000 liters. In other examples, the volume of the vessel is about 3-6 liters.

The disclosed bioreactors also include at least one opening (for example, at least 1, 2, 3, 4, 5, 6, 7, 8, 9, 10, or more openings) in the vessel that is connected to a means for introducing a gas (for example, for introducing oxygen or carbon dioxide into a liquid in the vessel). In some examples, the means for introducing a gas includes a gas sparger or diffuser. One of skill in the art can select appropriate gases and/or nutrients and their concentrations based on the organism, cell, or tissue present in a bioreactor of the disclosure. The sparger or diffuser may be inserted in the vessel through the opening, attached directly to the opening, or indirectly attached, for example by a tube or other connector.

In some embodiments, the at least one opening in the vessel is located on a side of the vessel. The opening is located below the level of the scaffold placed in the vessel. In some examples, the opening is within about 0.1 to 0.95 of the distance between the bottom of the scaffold and the bottom of the vessel. In some embodiments, the opening is placed so it is substantially aligned with a scaffold, for example, in embodiments where the interior of the scaffold provides the riser (e.g., FIGS. 1B, 6A-6C. 7A and 7B, and 9A-9C). In other embodiments, the opening is placed so that it is horizontally displaced relative to a scaffold, for example, in embodiments, where the interior of the scaffold provides the downcomer (e.g., FIGS. 15A and 15B).

In other embodiments, the opening is located on the bottom of the vessel. In some embodiments, the opening is placed so it is substantially directly underneath a scaffold, for example, in embodiments where the interior of the scaffold provides the riser. In other embodiments, the opening is placed so that it is displaced relative to a scaffold, for example, in embodiments, where the interior of the scaffold provides the downcomer.

In some embodiments, the vessel further includes one or more additional openings or ports for air venting, adding or removing cell culture medium and/or cells, sensor placement, and so on. In some examples, the opening includes a cap, lid, valve, or other replaceable closure, such that the opening can be closed or substantially closed during operation of the bioreactor.

II. Description of Particular Embodiments

FIG. 1 shows an example of a single scaffold Accordion Air Loop bioreactor (FIG. 1A) and a schematic illustration of its operation (FIG. 1B). Air bubbles coming from the gas sparger cause the liquid in the immediate vicinity to have an elevated gas hold up, causing the liquid's relative density to drop and causing the liquid to rise through the scaffold, which serves as a riser. When the lower-density liquid arrives at the surface of the liquid, the air bubbles disengage from the liquid and the air escapes into the atmosphere. The resulting higher-density or heavier liquid then sinks to the bottom outside the scaffold through the downcomer, causing a circular or looped flow around and through the scaffold.

FIG. 2 illustrates some differences between an exemplary Accordion Air Loop bioreactor embodiment (FIG. 2B) and a conventional airlift bioreactor (FIG. 2A) in terms of their geometric configuration and flow patterns. The Accordion Air-Loop as shown is equipped with a zigzag Accordion scaffold serving as a riser, as opposed to the straight vertical riser of the conventional Airlift bioreactor. The use of the Accordion scaffold alters the patterns of the liquid flow within and outside the riser, causing the liquid to become more well-mixed and significantly enhancing the efficiency of the mass transfer of gases from the sparged bubbles into liquid medium for example, compared to the conventional airlift design (described in Example 1, below).

Figure 4:
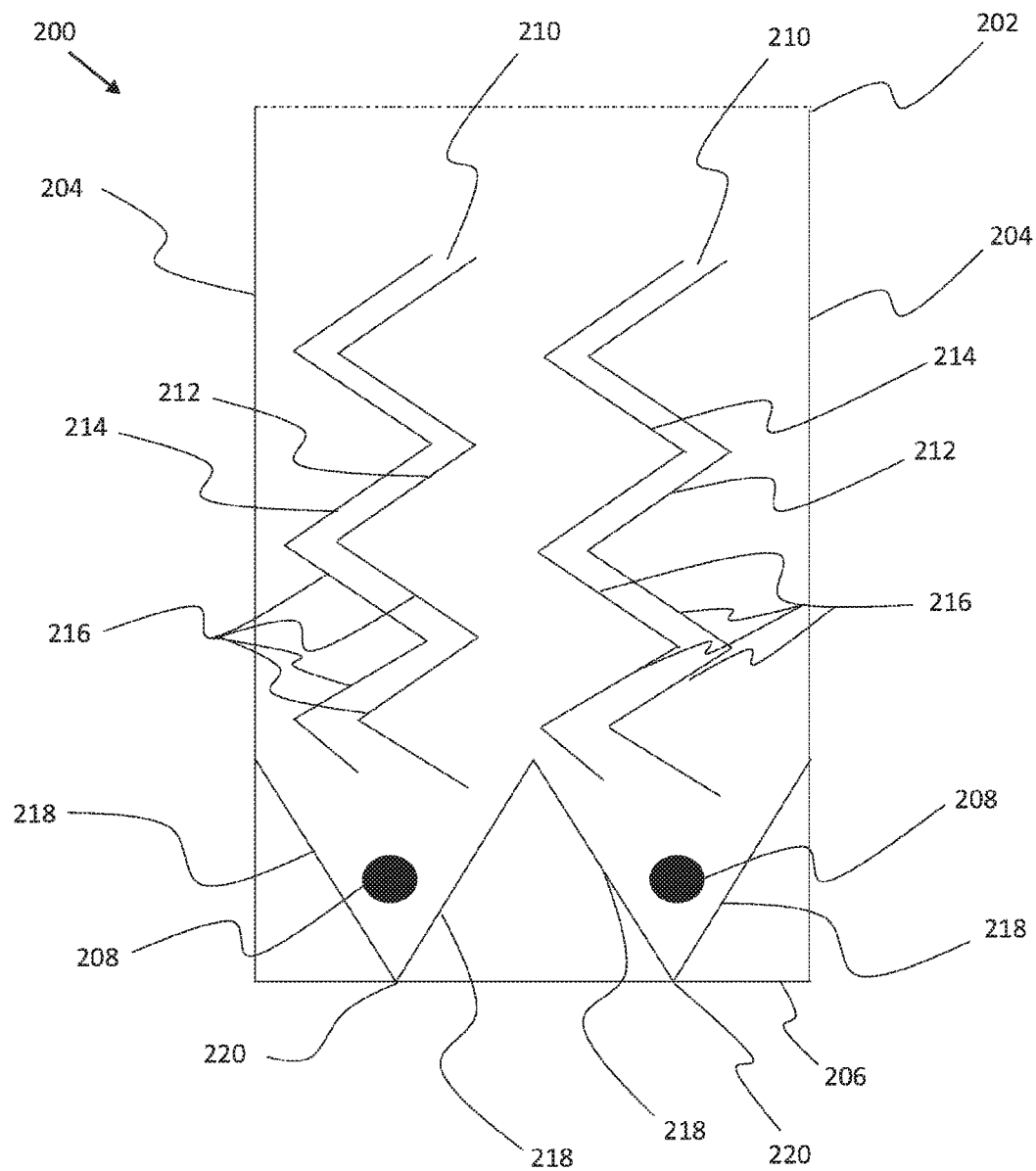
FIG. 4 illustrates an exemplary embodiment of a double air-loop accordion bioreactor.

FIGS. 3 and 4 illustrate exemplary embodiments of air-loop accordion bioreactors. As illustrated in FIG. 3, bioreactor 100 includes a vessel 102 having sides 104 and a bottom 106. Vessel 102 optionally includes a top, in some examples. Vessel 102 includes an opening 108, through which gas can be introduced, for example using a sparger or other means to introduce gas. In some examples the means for introducing a gas (such as a sparger) is inserted into the vessel through opening 108. In other examples a means for introducing a gas is connected to opening 108 externally, for example directly or through a connector or tubing. Air-loop accordion bioreactor 100 includes a scaffold 110 inside vessel 102, having a first sheet 112 and a second sheet 114. First sheet 112 and second sheet 114 are spaced apart and are substantially parallel to one another. Each of first sheet 112 and second sheet 114 include multiple sections 116 oriented at alternating angles. In particular embodiments, bioreactor 100 also includes a v-shaped or "funnel" structure 118 that starts at sides 104 and comes to a point 120 at the bottom 106 of vessel 102 below opening 108. This v-shaped portion directs the downcomer flow toward the means for introducing a gas (such as a sparger), which creates upward flow through the riser. This structure helps reduce or eliminate possible dead volumes in the vessel in which cells could be trapped and/or settle.

FIG. 4 illustrates an exemplary "double" bioreactor 200. Bioreactor 200 includes a vessel 202 having sides 204 and a bottom 206. Vessel 202 optionally includes a top, in some examples. Vessel 202 includes two openings 208, through which gas can be introduced, for example using a sparger or other means to introduce gas. Bioreactor 200 includes two scaffolds 210 inside vessel 202, each having a first sheet 212 and a second sheet 214. First sheet 212 and second sheet 214 are spaced apart and are substantially parallel to one another. Each of first sheet 212 and second sheet 214 include multiple sections 216 oriented at alternating angles. In particular embodiments, bioreactor 200 also includes v-shaped or "funnel" structures 218 that start at sides 204 and come to a point 220 at the bottom 206 of vessel 202. In this exemplary "double" bioreactor, each opening 208 is above the point 220 of a separate v-shaped structure.

Figure 5A:
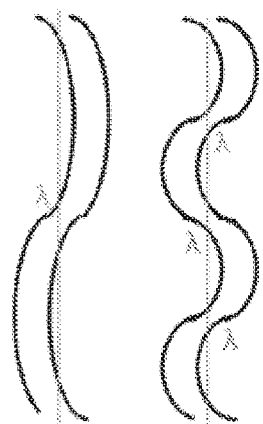
FIGS. 5A-5D are a series of schematic diagrams of Accordion Air Loop scaffolds, including curved (FIG. 5A), mixed angular and straight (FIG. 5B), zigzag (FIG. 5C) configurations with varying angles or angles of curvature.
Figure 5B:
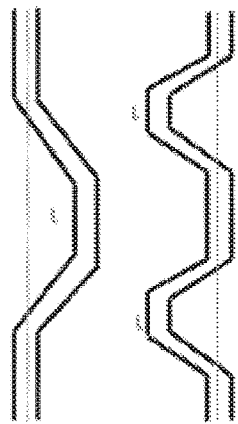
Figure 5C:
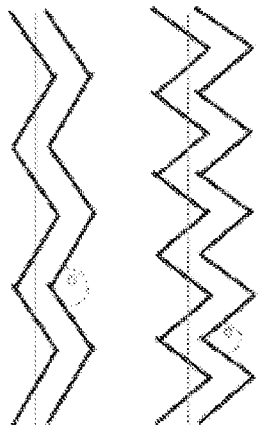
Figure 5D:
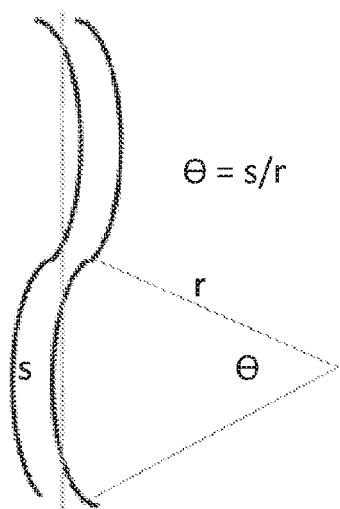

FIGS. 5A-5D illustrate various geometric configurations of the Accordion scaffold that can be used in embodiments of the disclosed bioreactors. For example, in some embodiments, the scaffold has two or more curved portions (FIG. 5A), while in other embodiments, the scaffold has alternating straight and angled portions (FIG. 5B). In still further embodiments, the scaffold has alternating angled portions (FIG. 5C). In each embodiment, the pitch angle of the sections of the scaffold (or the angle of curvature if the scaffold has a curved configuration) may be varied, as illustrated in FIGS. 5A-5D.

The bioreactors disclosed herein can have two, three, or more Accordion scaffolds (such as two or more zig-zag, mixed, and/or curved configuration scaffolds) in a single vessel in some embodiments, as illustrated in FIGS. 6A-6E and FIGS. 7A-7C. The use of multiple Accordion scaffolds is believed to further enhance the flow patterns and gas mass transfer in the liquid medium. For an Accordion Air Loop with a single Accordion scaffold, at least one portion of the scaffold has a pitch angle (angle relative to horizontal) of greater than 0°, for example as shown in FIG. 6A. For an Accordion Air Loop with two or more Accordion scaffolds, however, the pitch angle of the scaffolds may be 0°, for example as shown in FIG. 6C, or may include at least one portion with a pitch angle greater than 0° (FIG. 6B).

Figure 9A:
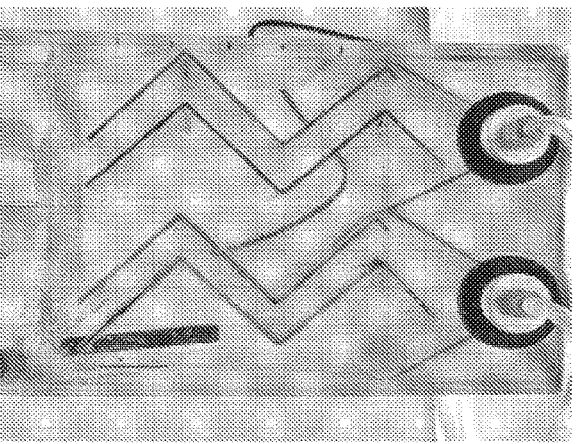
FIGS. 9A-9D are a series of digital images of Accordion Air Loop bioreactors constructed with polycarbonate sheets (FIGS. 9A-9C) and using a glass vessel and metal scaffolds (FIG. 9D).
Figure 9B:
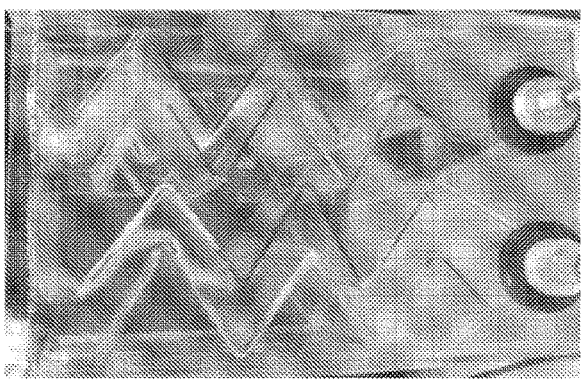
Figure 9C:
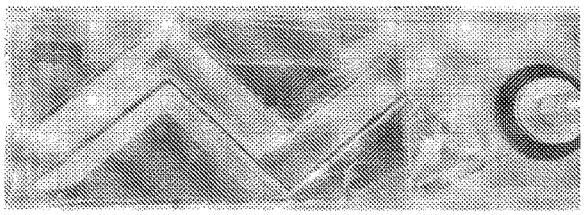
Figure 9D:
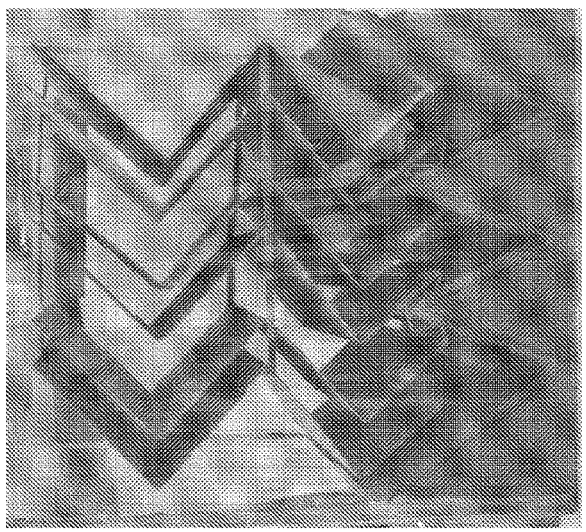

Prototypes of the Accordion Air Loop were constructed using polycarbonate (FIGS. 9A-9C). An exemplary Accordion Air Loop with three Accordion scaffolds was made using a glass vessel and metal scaffolds (FIGS. 7A, 7B, and 9D). While the bioreactor vessels used were rectangular boxes, the vessel for the Accordion Air Loop may also be a square box or cylindrical in shape, or any other desired shape, which can be selected by one of skill in the art.

Figure 15A:
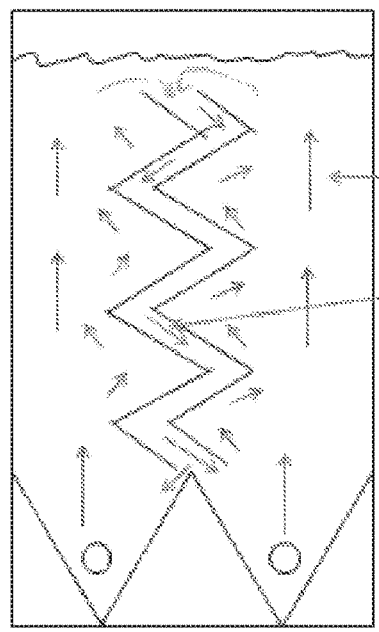
FIGS. 15A and 15B are a pair of schematics showing exemplary Accordion Air Loop bioreactors with the spargers located so that the flow rises outside of the scaffold and the downcomer is through the interior of the scaffold. Exemplary single scaffold (FIG. 15A) and double scaffold (FIG. 15B) embodiments are illustrated.
Figure 15B:
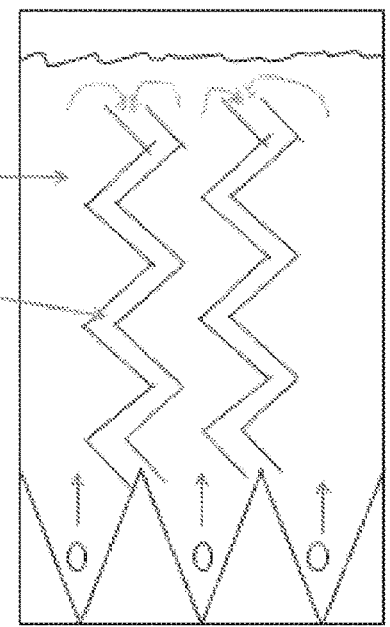
Figure 16A:
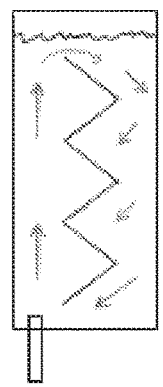
FIGS. 16A-16D are a series of schematics showing exemplary "external" airlift Accordion Air Loop bioreactors.
Figure 16B:
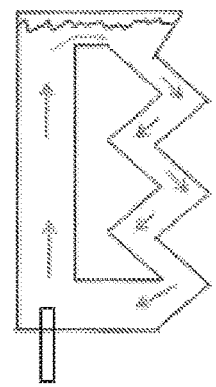
Figure 16C:
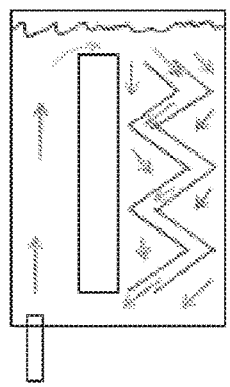
Figure 16D:
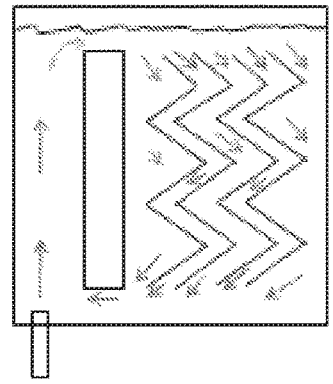

FIGS. 15A and 15B show configurations of the Accordion Air Loop Bioreactor where openings for introducing gas are located offset from the Accordion scaffold (e.g., straddling the scaffold) so that the resulting flow rises outside of the scaffold (riser) and goes down through the interior of the scaffold (downcomer).

FIGS. 16A-16D show various external-airlift configurations of the Accordion Air Loop Bioreactor. The presence of a horizontal arm or bridge at the top of the bioreactor (FIGS. 16B-16D) allows the air bubbles to disengage from the liquid more completely, resulting in denser liquid that sinks faster to the bottom (e.g., higher flow velocity) through the downcomer side of the bioreactor. The arm or bridge effectively separates the bioreactor into two sections, a riser section, which is on the same side of the bridge or arm as the sparger and a downcomer section, which is on the other side of the bridge or arm and includes the scaffold(s). In some examples (such as FIGS. 16C and 16D), the downcomer includes liquid flow through the scaffold (between the first and second sheets), outside the scaffold, and (in embodiments with two or more scaffolds) between the scaffolds.

III. Methods of Culturing Cells in an Air Accordion Bioreactor

Disclosed herein are methods of culturing cells in a bioreactor utilizing embodiments described herein. In one embodiment, the method includes incubating a suspension of cells in a nutrient solution in a bioreactor of the present disclosure. In another embodiment, the method includes cells in culture medium. The methods include batch culture, semi-continuous culture, or continuous culture of the cell and/or organism of interest. During operation of the bioreactor, samples can optionally be collected through one or more openings in the vessel.

In some examples, mixing and aeration of the cell suspension or culture medium containing cells or tissue is provided by one or more gas spargers or diffusers connected to the opening in the vessel. The gas bubbling from the sparger or diffuser through the culture medium provides mixing (for example, through riser and downcomer flow) and gas transfer. The gas flow rate is adjusted to provide adequate mixing and aeration for cell growth. In some examples, the gas flow rate provides mixing such that the cells in the culture medium do not appreciably settle, but remain in suspension. The gas flow rate is adjusted to provide sufficient mixing, without causing substantial damage to the cells, for example from shear stress. In particular examples, the methods include sparging the cell suspension or the culture medium with a mixture of 5% $CO_2$/95% air. Appropriate gas mixtures can be selected by one of the skill in the art based on the type of cell that is being cultured. One of skill in the art can also select appropriate gas flow rates for the particular cell culture (such as the particular cells being cultured). Exemplary gas flow rates include about 0.05 to 2 gas volume flow per unit of liquid volume per minute (vvm), for example, about 0.1 to 0.5 vvm, about 0.3 to about 1.5 vvm, or about 0.5 to 1 vvm. In particular examples, the gas flow rate is about 0.1 vvm or about 0.3 vvm. However, one of skill in the art will recognize that the gas flow rate selected depends in part on the volume of the vessel. For example, bioreactor with a larger volume will require a higher gas flow rate than that in the smaller volume reactors shown in Examples 1-4 herein.

During operation, the disclosed bioreactors include a headspace between the surface of the liquid in the vessel and the top of the scaffold. In some examples, the headspace is about 0.5 to 2 inches. In particular examples, the headspace is about 0.5 inches or about 1 inch. However, one of skill in the art will recognize that the headspace selected depends in part on the size of the bioreactor. Thus, in some examples, the headspace is determined relative to the sum of the height of the scaffold (h) and the headspace width ($W_h$) in the form of the ratio $W_h/(h+W_h)$. In some non-limiting examples, the ratio $W_h/(h+W_h)$ is about 0.05 to 0.75 (for example, about 0.06 to 0.5 or about 0.1 to 0.3).

In some embodiments, the method includes exposing the bioreactor, and the culture in the bioreactor, to a light source, for example for culture of photosynthetic cells, such as algae. In some examples, the light source is natural sunlight. For example, the bioreactor may be placed outdoors or in a greenhouse where it is exposed to natural sunlight. In this example, the culture is exposed to natural light/dark cycles, which vary in length according to latitude and season. In other examples, the bioreactor and culture is exposed to an artificial light source (for example, incandescent, fluorescent, or halogen lamps, or light emitting diodes). If the light source is an artificial light source, the method may include alternating periods of light and dark. In one example, the bioreactor is exposed to light for 12 hours of a 24 hour cycle.

In some examples, the wavelength of the light source (such as an artificial light source) is selected to promote optimal growth of the organism or cell type in culture in the bioreactor. In some examples, the wavelength of the light source includes or consists of photosynthetically active radiation (for example, wavelengths of light between about 400-700 nm). In other examples, the wavelength of the light source is selected to induce or increase synthesis of one or more compounds of particular interest by the organism or cell in culture. For example, synthesis of anthocyanin is induced by UV-B light (such as about 280-300 nm). One of skill in the art can select appropriate lights or wavelengths for culture of cells and/or production of compounds of interest, for example to maximize cell growth or production.

In other embodiments, the methods do not include exposing the culture in the bioreactor to light (for example, for heterotrophic cell culture). For example, the vessel (for examples, at least the sides and top of the vessel) can be made of opaque material, such that the cells and other components in the vessel are not exposed to light or are substantially not exposed to light during culturing. The culture may be exposed to light at the beginning and end of the culture period and may also be exposed to light for short times (for example, less than 15 minutes, less than 10 minutes, or less than 5 minutes) periodically during the culture period, for example to collect samples or add liquid, culture medium, or other components to the system.

In some examples, the angle of each portion of the bioreactor disposed on the horizontal supports relative to the vertical axis is selected to optimize the exposure of the chamber (and the culture within) to incident light. In some examples, the angle is selected such that the irradiance is about 80 to 500 µmol/m$^2$s. One of skill of the art can select an appropriate irradiance range, based on the cell or organism that is in culture in the bioreactor. In some examples, an irradiance of about 80-300 µmol/m$^2$s is selected if microalgae cells are in culture. In other examples, an irradiance of about 300-400 µmol/m$^2$s is selected if plant cells are in culture.

In some examples, the methods include regulating the temperature of the culture. Means for temperature regulation are well known to one of skill in the art. In one example, the bioreactor is in an enclosed area (such as a greenhouse) which is heated or cooled to maintain a selected temperature or range of temperatures. In other examples, the temperature of the culture may be regulated by a temperature regulation device in the culture medium or around the bioreactor. Such devices include heating or cooling jackets or heat exchangers. In particular examples, heat is provided at night in order to maintain the temperature of the culture in an optimal range for growing the culture. In other examples, cooling is provided during the day (particularly at times of day or seasons with high solar radiation) in order to maintain the temperature of the culture in an optimal range. One of skill in the art can select appropriate temperature ranges for the particular cell or organism in culture and determine the need for heating or cooling to maintain the selected temperature range.

In some embodiments, the method also includes harvesting the culture. The culture may be harvested when a selected parameter is reached, for example a time point (for example, at least about 6, 12, 24, 36, 48, 72, 96, or more hours of culture), cell density (for example, at least about $10^3$, $10^4$, $10^5$, $10^6$, or more cells per milliliter), or optical density of the culture (for example, absorbance of at least about 0.5, 1.0, 1.5, 2, 2.5, or more at a selected wavelength). One of skill in the art can select appropriate parameters or time points for culture harvest, based on the organism or cell type being cultured.

Methods for harvesting cells are well known to one of skill in the art. In some examples, the entire culture is harvested. In other examples, a portion of the culture is retained for use as inoculum for continued culture production. For example, culture is stored for use as an inoculum and water or culture medium is subsequently added to the bioreactor to start the new culture batch. In some examples, the culture stored for inoculum use is about 100 ml to about 100 liters (such as about 1-50 liters, 10-75 liters, 25-75 liters, or about 30-40 liters). In other examples, a proportion of the culture is retained for inoculation of the new culture, for example about 10-50% of the total harvested culture volume (such as about 10-40%, 10-35%, 20-50%, 20-40%, 30-35%, or about 33% of the total harvested culture volume). The volume or percentage of the culture needed for use as inoculum can be determined by one of skill in the art, for example, based on the cell or organism in culture, the density of the culture at harvesting, and the total volume of liquid that will be inoculated.

The bioreactors and methods disclosed herein are suitable for culturing a wide variety of organisms or cells, including, but not limited to algae (such as microalgae and/or macroalgae). In some examples, the algae species include, but are not limited to *Chlorella* (such as *Chlorella vulgaris*), *Chlamydomonas* (such as *Chlamydonmonas reinhardtii*), *Chaetoceros, Spirulina* (such as *Spindlina platensis*), *Dunaliella*, and *Porphyridum*. In particular examples, the algae species include algae useful for production of biofuels or other compounds (such as polyunsaturated acids, pigments, or phytochemicals, for example, for nutritional supplements). In some examples, the algae include *Akistrodesmus, Arthrospira, Botryococus braunii, Chlorella* (such as *Chlorella* sp. or *Chlorella protothecoides*), *Crypthecodinium* (such as *Crypthecodinium cohnii*), *Cyclotella, Dunaliella tertiolecia, Gracilaria, Hantzschia, Haemalococcus* (such as *Haematococcus pluvialis*), *Monodus* (such as *Monodus subterraneous*), *Nannochloris, Nannochloropsis, Neochloris oleoabundans, Nitzschia, Phaeodactylum, Pleurochrysis carterae* (also called CCMP647), *Porphyridium, Sargassum, Scenedesmus* (such as *Scenedesmus obliquus*), *Schiochytrium, Stichococcus, Tetraselmis suecica, Thalassiosira pseudonana, Thraustochytrium roseum*, and *Ulkenia* sp. In one example, the algae species is *Botryococcus braunii*.

The bioreactors and methods disclosed herein are also suitable for culturing any cells that can be grown in suspension, including but not limited to, microalgae (as discussed above), macroalgae, bacteria (e.g., *Escherichia coli, Bacillus subtilis*, or *Corynebacterium*), cyanobacteria (e.g., *Synechococcus* or *Synechocystis*), fungi (e.g., *Saccharomyces cerevisiae, Kluyveromyres lactis*, or *Pischia pastoris*), insect cells (e.g., *Spodoptera frugiperda* cells (such as Sf9 or Sf21 cells) or *Trichoplusia ni* cells (such as High Five™ cells)), plant cells (such as *Arabidopsis thaliana* cells, *Nicotiana tabacum* cells, or *Taxus* cells), or mammalian cells (such as Chinese hamster ovary (CHO) cells). In one example, the bioreactors and methods disclosed herein are useful for culturing algae for the production of fatty acids for synthesis of biofuels. In other examples, the bioreactors and methods disclosed herein are useful for culturing cells for the production of other natural products (such as taxols, pigments, or dietary supplements) or recombinant proteins.

The present disclosure is illustrated by the following non-limiting Examples.

EXAMPLE 1

Parameters Affecting Liquid Mass-Transfer Coefficient

This example describes various configurations of bioreactors and the effect of design factors on liquid mass-transfer coefficient.

Each of the bioreactors was constructed from clear LEXAN® polycarbonate sheets of two different thicknesses, of 0.25 inch for the external walls of the bioreactors, and of 0.093 inch for the internal accordion designs and airlift design. Two polyethylene bioreactors were used in the experiments, which had a volume of 6.0 L and 3.0 L. A third larger 9.0 L prototype bioreactor was built using glass and steel, but was not used for the experimentation. The width of the riser was set to 0.5 inch, in order to match the diameter width of the stainless steel gas diffusers. The sheets were cut using a band saw to specific dimensions and were then fixed together using Methyl Ethyl Ketone (MEK) Plastic Weld. The accordion scaffolding and the angled funnel-like base of the bioreactors were bent using a brake similar to bending sheet metal. The cylindrical gas diffusers were 6.0" inches long and 0.5" inch in diameter, custom made using 5.0 micron (μm) porous stainless steel with a standard male pipe threading end and manufactured from MOTT Inc. (Pennsylvania, US).

Figure 10A:
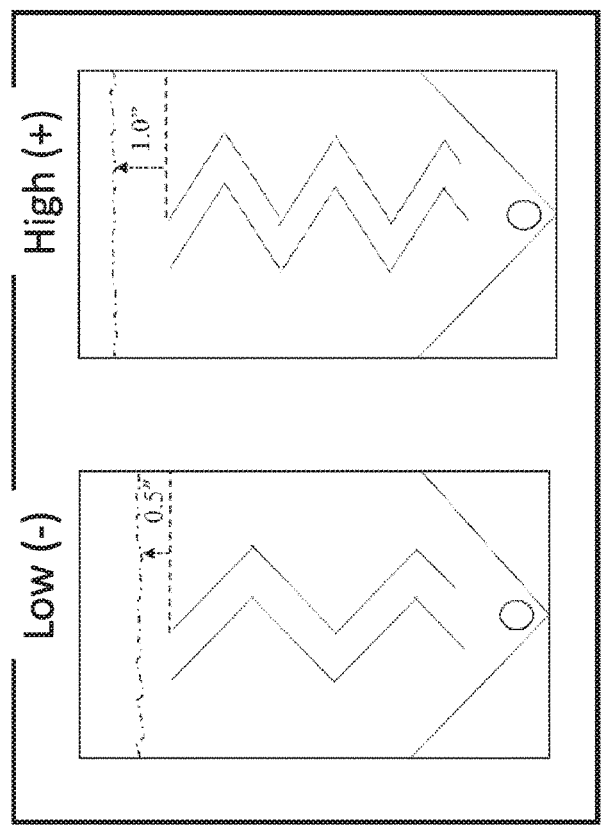
FIGS. 10A and 10B are a pair of diagrams showing different levels of pitch angle (FIG. 10A) or width of headspace (FIG. 10B) used to determine liquid mass-transfer coefficient (kla) for oxygen in water in the Accordion Air Loop bioreactor).
Figure 10B:
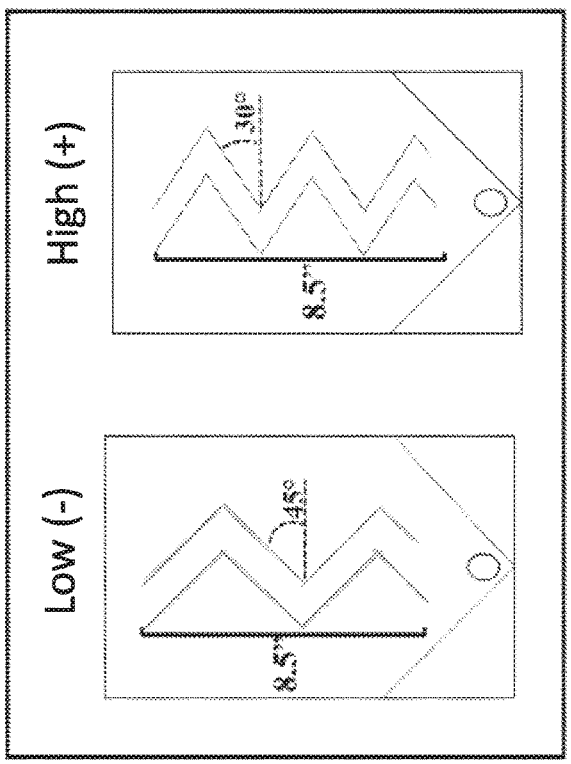

Accordion Air Loop bioreactors were constructed to assess four selected design factors—pitch angle, scaffold type, gas flow rate, and width of headspace. Each factor was assigned two levels each (Table 1), forming a $2^4$ factorial design, and yielding a total of 16 treatments. The different levels of pitch angle and width of headspace are illustrated schematically in FIGS. 10A and 10B.

TABLE 1

Design factors and their levels for the Accordion Air Loop kla experiment.

| Design Factors | | High level (+) | Low level (−) |
|---|---|---|---|
| A | Pitch angle | 30° (more zigzags) | 45° (less zigzags) |
| B | Accordion scaffold | Double | Single |
| C | Gas flow rate | 0.3 vvm | 0.1 vvm |
| D | Width of headspace | 1.0 inch | 0.5 inch |

Figure 11:
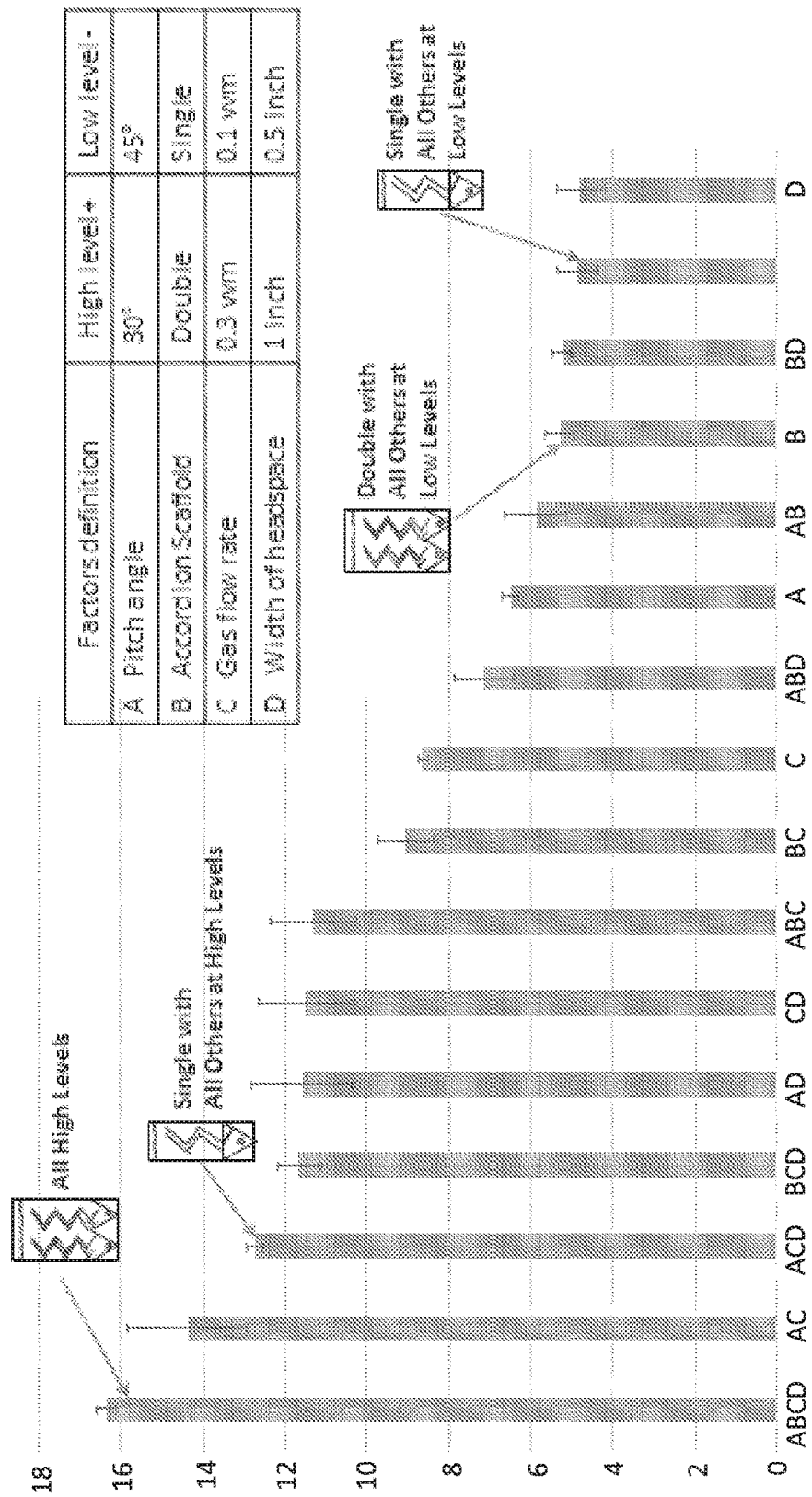
FIG. 11 is a graph showing values of kla [(1/s)×1000] for the varying design factors shown in Table 1 (below).

The results of the kla experiments, shown in FIG. 11, indicated that varying the levels of the four factors resulted in statistically significant kla values, signifying that the factors and their levels had significant impact on the efficiency of the gas mass transfer in the liquid medium. FIG. 11 shows that the highest kla was achieved by the treatment where all four factors were set at high levels (ABCD), corresponding to the Accordion Air Loop with double Accordion scaffolds plus high settings for pitch angle, gas flow rate, and width of headspace. For the Accordion Air Loop with a single Accordion scaffold, setting all the other factors at high levels (ACD) resulted in the third highest kla. The highest kla obtained for the Accordion Air Loop with a single Accordion scaffold, however, corresponded with the treatment where the pitch angle and gas flow rate were both set at high levels and the width of headspace was set at low level (AC).

Figure 12:
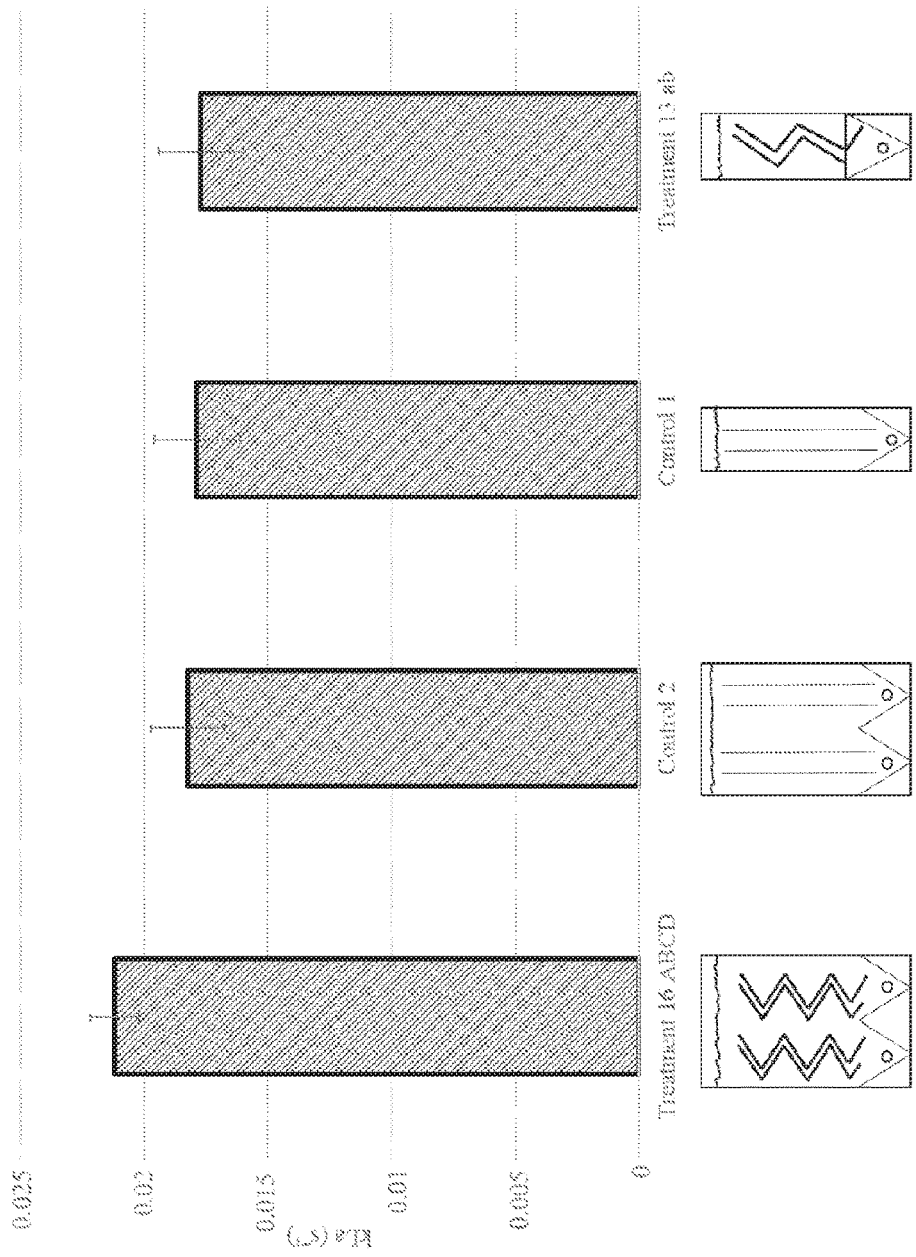
FIG. 12 is a graph showing kla (1/s) at a high gas flow rate (0.3 vvm) for the illustrated configurations. Treatment 16 ABCD: two Accordion scaffolds with pitch angle 30° and width of headspace 1 inch (high levels); Control 2: two straight risers with width of headspace 1 inch (high level); Control 1: one straight riser and width of headspace 1 inch (high level); and Treatment 13 ab: single Accordion scaffold with pitch angle 45° (low level) and width of headspace 1 inch (high level).

A second kla experiment was conducted to compare the Accordion Air Loop Bioreactors versus a conventional Air Lift bioreactor. At a high gas flow rate of 0.3 vvm, the results showed that the kla for the Accordion Air Loop with double Accordion scaffolds significantly exceeded those for the two controls and the Accordion Air Loop with a single Accordion scaffold (FIG. 12). The kla values for the Accordion Air Loop with a single Accordion scaffold and the two controls were statistically indistinguishable.

Figure 13:
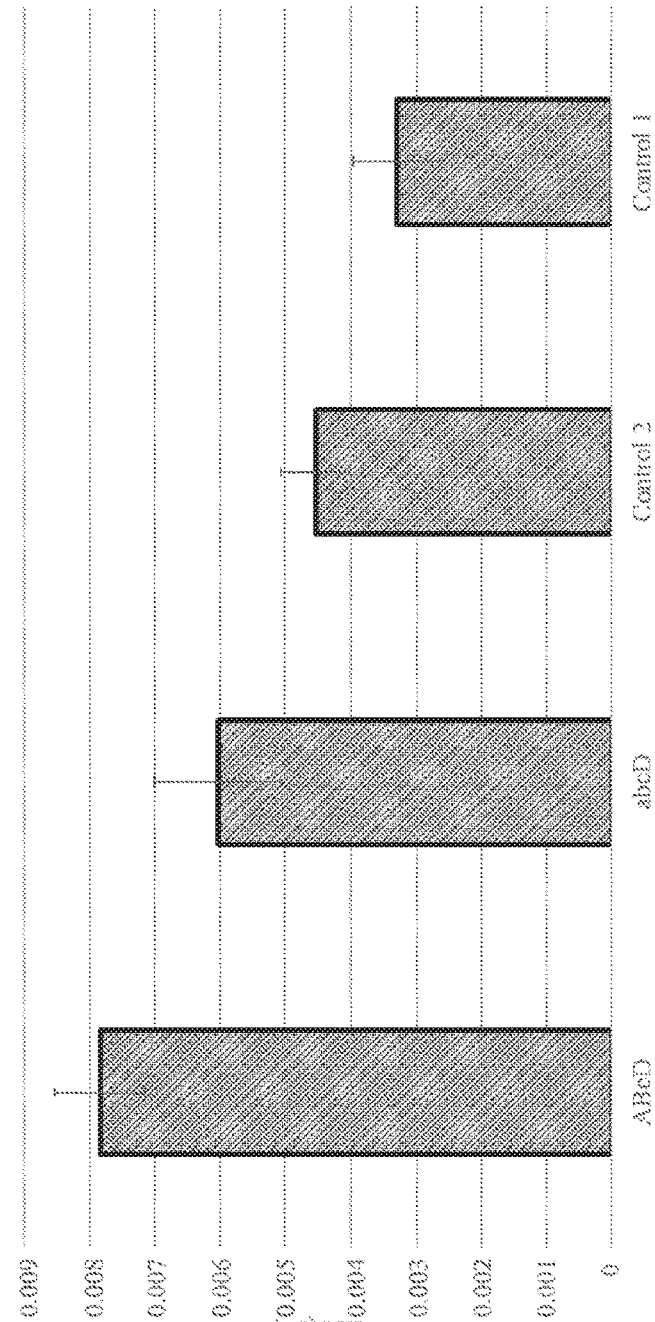
FIG. 13 is a graph showing kla (1/s) at a low gas flow rate (0.1 vvm) for the illustrated configurations. ABCD: two Accordion scaffolds with pitch angle 30° and width of headspace 1 inch (high levels); abcD: single Accordion scaffold with pitch angle 45° (low level) and width of headspace 1 inch (high level); Control 2: two straight risers with width of headspace 1 inch (high level); and Control 1: one straight riser and width of headspace 1 inch thigh level).

At the low gas flow rate of 0.1 vvm, the results showed that the kla values for the Accordion Air Loop with double Accordion scaffolds remained significantly greater than those for the two controls and the Accordion Air Loop with a single Accordion scaffold (FIG. 13). The kla value for the Accordion Air Loop with a single Accordion scaffold, however, significantly exceeded those for the two controls (FIG. 13).

In summary, treatments with high gas flow rate of 0.3 vvm consistently yielded higher kla values (approximately 0.010/s and greater) than did treatments with low gas flow rate of 0.1 vvm (less than 0.010/s). The highest kla value (0.019/s) was obtained in treatment ABCD which used double zig-zag scaffolds with an acute pitch angle of 30°, a head space of 2.54 cm (1 in), and a high gas flow rate of 0.33 vvm.

EXAMPLE 2

Algal Cell Culture in Accordion Air Loop Bioreactor

This example describes culture of algal cells in an Accordion Air Loop bioreactor.

Figure 14A:
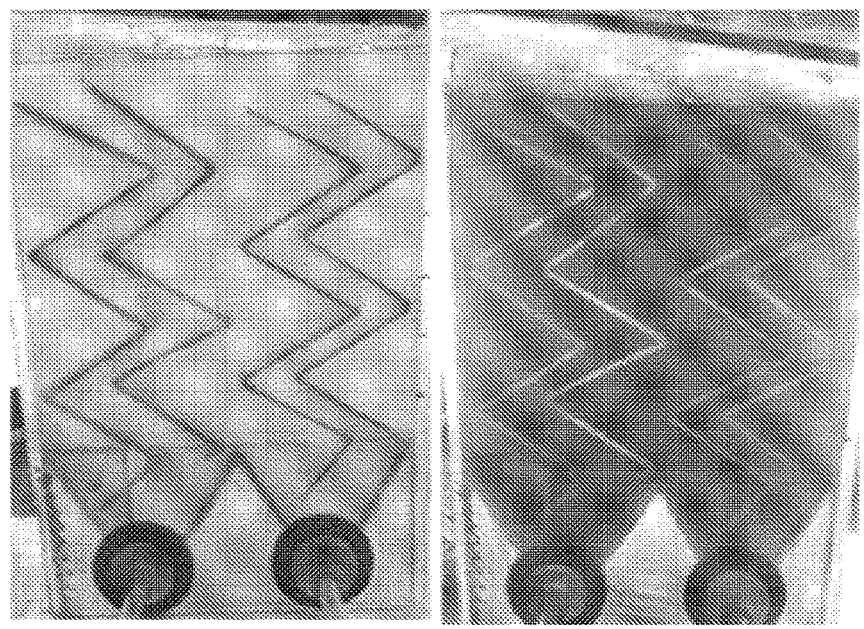
FIGS. 14A and 14B are a series of digital images showing growth of *Scenedesmus obliquus* in a double scaffold Accordion Air Loop bioreactor (FIG. 14A) and a single scaffold Accordion Air Loop bioreactor (FIG. 14B).
Figure 14B:
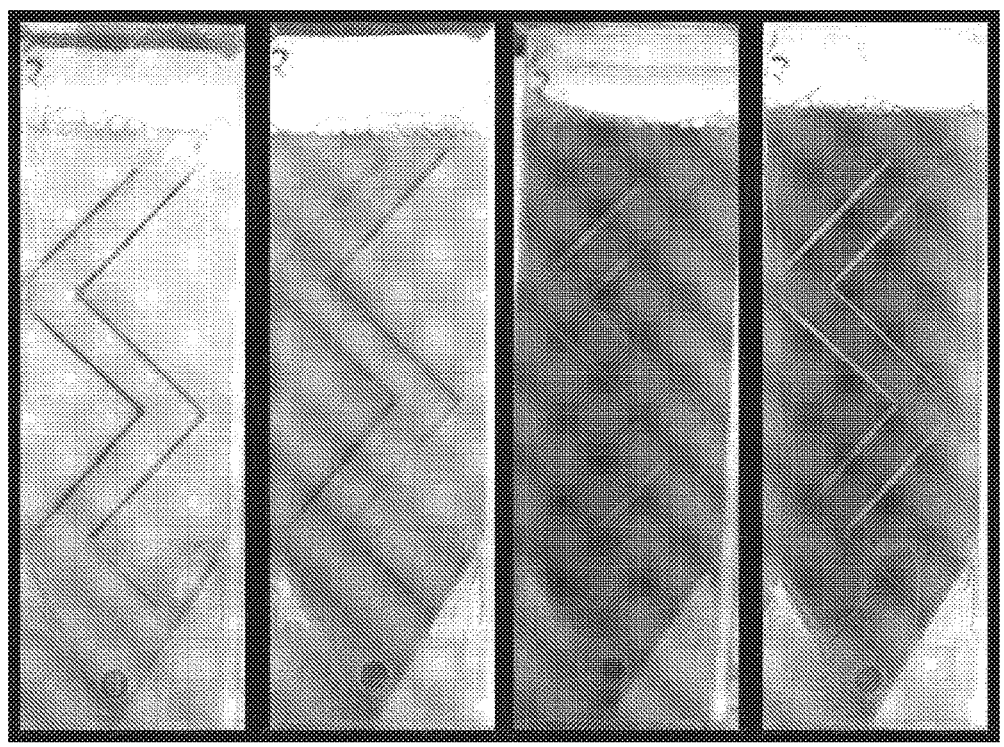

Both double scaffold (FIG. 14A) and single scaffold (FIG. 14B) Accordion Air Loop bioreactors were successfully used for photoautotrophic cultivation of the green microalga *Scenedesmus obliquus*. The cells were grown for 8 days at 25° C. with 100 μmol/m$^2$ photon flux. Cells were grown in a bioreactor with a scaffold pitch of 30° with flow rate of 0.3 vvm and headspace of 0.5 inches (FIG. 14A) or with a scaffold pitch of 45° with flow rate of 0.1 vvm and headspace of 0.5 inches (FIG. 14B).

EXAMPLE 3

Liquid Mixing Time in Accordion Air Loop Bioreactor

This example describes mixing time at high and low gas flow rates in an Accordion Air Loop bioreactor.

The mixing time ($T_m$) measurements of each bioreactor was established by injecting a predefined amount of sodium chloride (NaCl) solution into each bioreactor (5 mL of 60 g L$^{-1}$ solution into the 3.0 L bioreactors and 10.0 mL of the same solution into the 6.0 L bioreactors) at a set location and measuring the electrical conductivity (EC) of the fluid. After the injection, the amount of time required for the NaCl concentration to come within 5% of equilibrium was measured for each of the bioreactors. The National Instruments Vernier Sensor DAQ USB Data Acquisition unit, teamed together with the Vernier Conductivity Probe and logger program was used to log the electrical conductivity and calculate the average $T_m$.

$T_m(\text{seconds}) = T_m = T_F - T_i$, where $T_F$=Time at 90% of Final NaCl Concentration and $T_i$=Initial Time at injection.

Figure 17A:
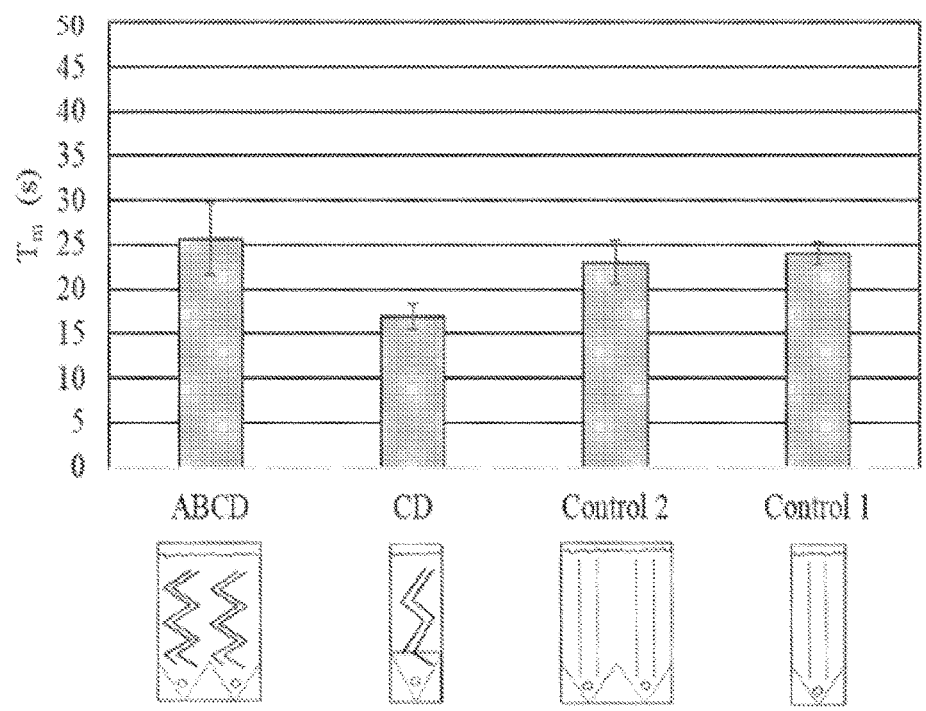
FIGS. 17A and 17B are graphs showing mixing time at high gas flow rate (0.3 vvm.
Figure 17B:
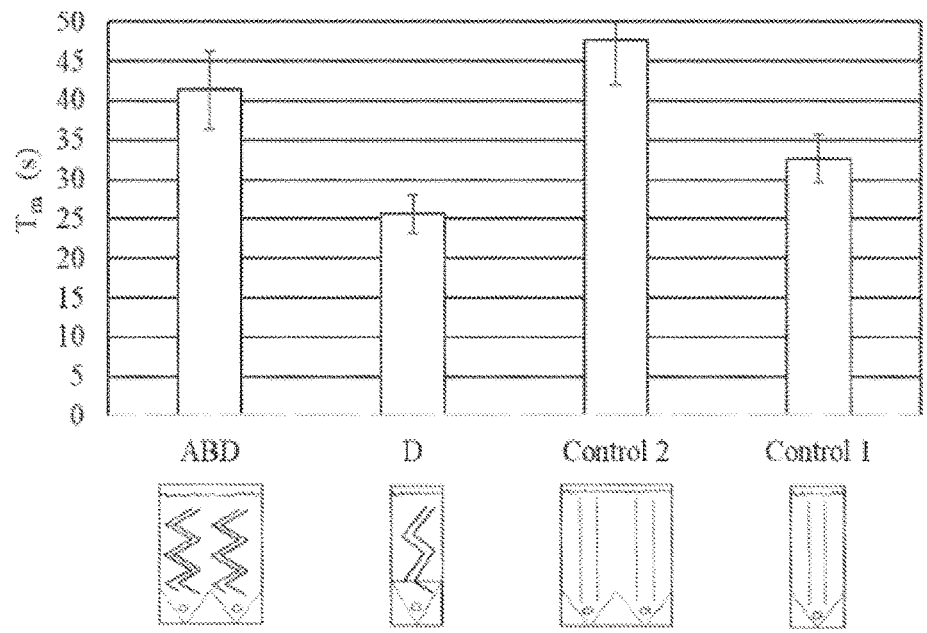

The mixing time values for the two treatments ABCD and CD as well as those for the single and double airlift controls, all operated at the high gas flow rate of 0.3 vvm (FIG. 17A), were consistently and significantly faster than the mixing time values for treatments ABD and D as well as those for the single and double airlift controls all operated at the low gas flow rate of 0.1 vvm (FIG. 17B). Experiments with high gas flow rate (0.3 vvm) consistently yielded fast (about 15 s or less) and medium (about 25 s) values of mixing time, whereas treatments with low gas flow rate (0.1 vvm) consistently yielded medium (about 25 s) and slow values (about 40 s) of mixing time. The fastest mixing time value (11 s) was obtained in treatment CD which used a single zig-zag scaffold with an obtuse pitch angle of 45°, a head space of 2.54 cm (1 in), and a high gas flow rate of 0.33 vvm.

EXAMPLE 4

Algae Cell Growth in Accordion Air Loop Bioreactor

This example describes growth of algae cells in an Accordion Air Loop bioreactor.

Each bioreactor was initially inoculated with a culture of *Scenedesmus obliquus* having an absorbance of 0.1 $OD_{750}$. Daily measurements of the cultures' dry weight were recorded from each condition (reactor configuration with high or low gas flow). Two separate 5 mL samples were taken each day and placed into 50 mL centrifuge tubes. Each sample was centrifuged at 4,000 rpm for 5 minutes, the media discarded and the pellet re-suspended in 20 mL of deionized water. This solution was then filtered through G6 category glass fiber circular filters and set in a drying oven overnight. Prior to filtration, the glass fiber filters were numbered and set inside an oven overnight to dry before being weighed. The biomass was calculated by taking the weight of the dry filter with the dry algae and subtracting the weight of the dry filter.

Figure 18A:
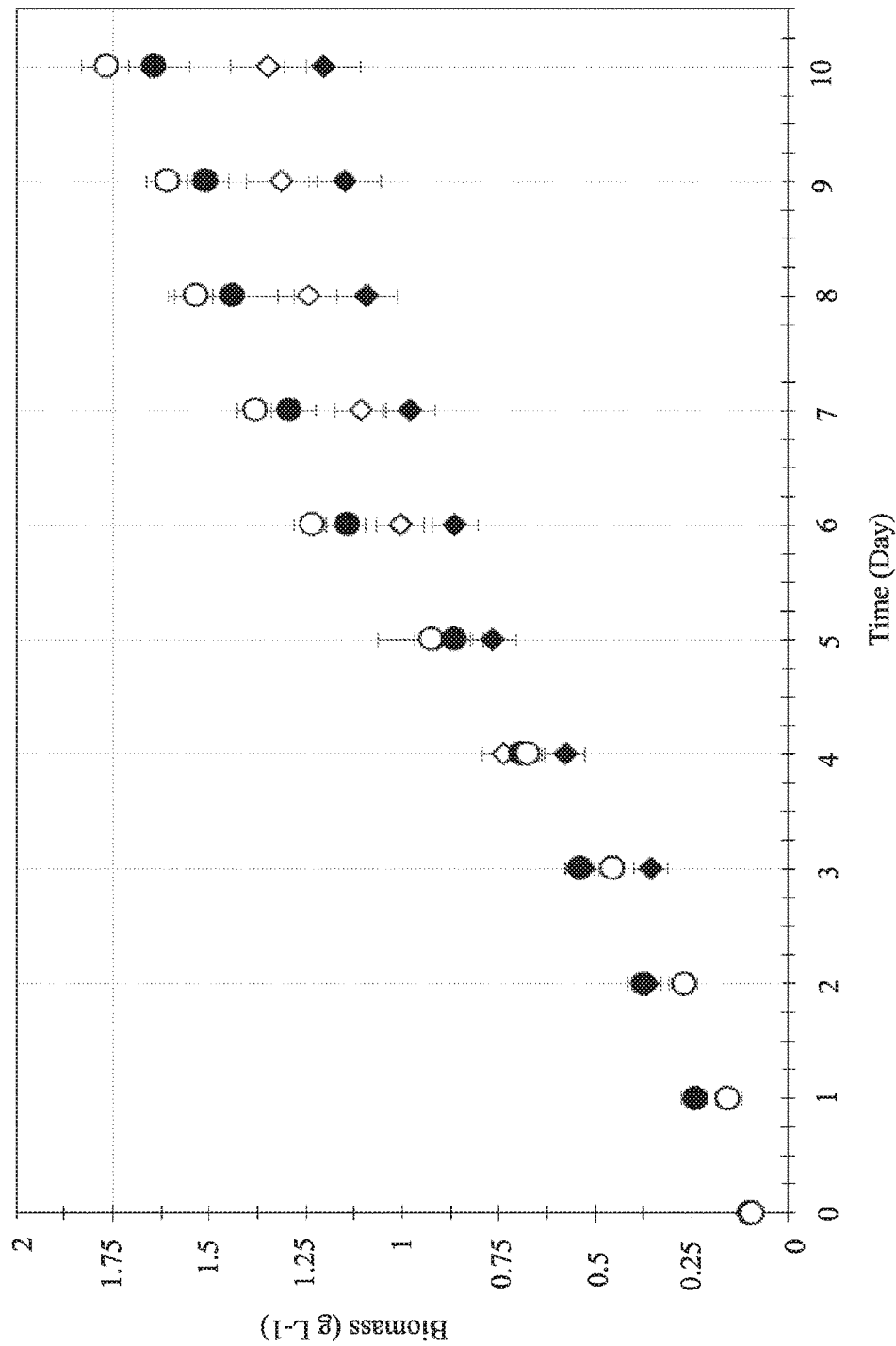
FIGS. 18A and 18B are graphs showing growth curves of *Scenedesmus obliquus* at high gas flow rate (0.3 vvm.
Figure 18B:
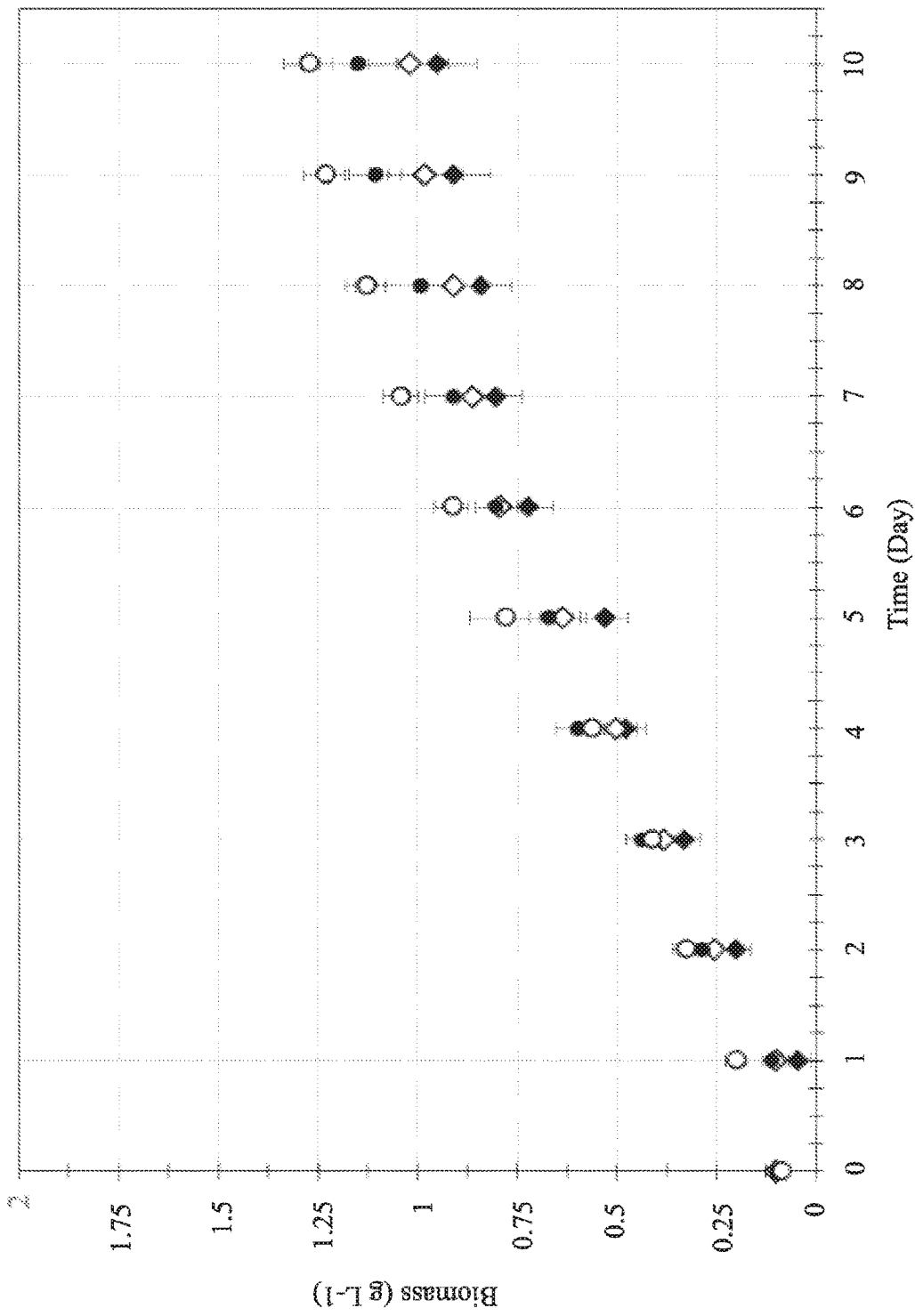

The algae biomass growths at high gas flow rate (0.3 vvm) in the two selected treatments of the double air-loop Accordion ABCD (1.21 g/L) and the single air-loop Accordion CD (1.64 g/L) significantly exceeded those in their respective controls at low gas flow rate (0.1 vvm) of the double air-loop Accordion ABD (0.95 g/L) and the single air-loop Accordion D (1.15 g/L), respectively (FIGS. 18A and 18B; Table 2). The algae biomass growths at high gas flow rate (0.3 vvm) in the double airlift control (1.34 g/L) and the single airlift control (1.87 g/L) significantly exceeded those at low gas flow rate (0.1 vvm) for the double airlift control (1.02 g/L) and the single airlift control (1.28 g/L), respectively (FIGS. 18A and 18B; Table 2).

TABLE 2

Comparison of final biomass concentrations of *Scenedesmus obliquus* in single and double air loop and air lift bioreactors

| Reactor | Low Gas Flow Final Biomass (g/L) | High Gas Flow Final Biomass (g/L) | Difference (g/L) |
| --- | --- | --- | --- |
| Double Airloop Accordion | 0.95 ± 0.06 | 1.21 ± 0.08 | 0.26 ± 0.12 |
| Double Airlift | 1.02 ± 0.06 | 1.34 ± 0.09 | 0.32 ± 0.15 |
| Single Airloop Accordion | 1.15 ± 0.09 | 1.64 ± 0.04 | 0.49 ± 0.13 |
| Single Airlift | 1.28 ± 0.04 | 1.87 ± 0.03 | 0.59 ± 0.07 |

Unexpectedly, the algae biomass growths at high gas flow rate in the single air-loop Accordion CD (1.64 g/L) and in the single airlift control (1.87 g/L) significantly exceeded those in the double air-loop Accordion ABCD (1.21 g/L) and in the double airlift control (1.34 g/L) (Table 2). In addition, the resulting algae biomass growth in the single airlift control (1.87 g/L) significantly exceeded that in the single air-loop Accordion CD (1.64 g/L). That the algae biomass growth in the double air-loop Accordion ABCD (1.21 g/L) and in the double airlift control (1.34 g/L) were significantly lower than that in the single airlift control (1.87 g/L) was inconsistent with predictions based on hydrodynamic data.

Figure 19A:
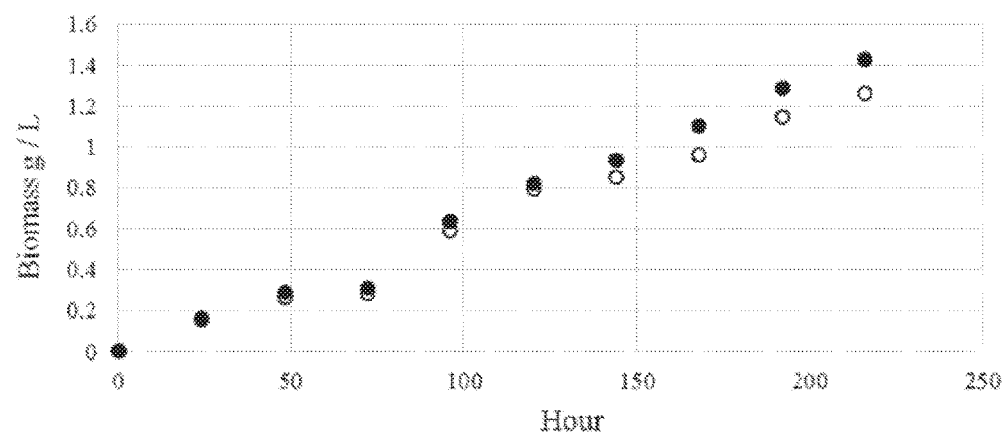
FIGS. 19A-19C are a series of graphs showing growth curves of *Scenedesmus obliquus* at high gas flow rate (0.3 vvm) in a double airlift accordion bioreactor (FIG. 19A), a double airlift bioreactor (FIG. 19B), or a single air-loop accordion bioreactor (FIG. 19C) before (open circles) or after (closed circles) adhering algae cells were gently removed from the scaffold surfaces.
Figure 19B:
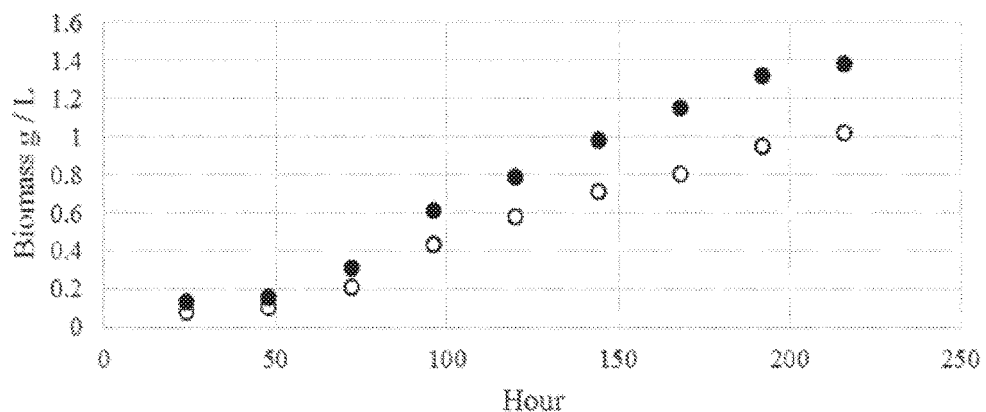
Figure 19C:
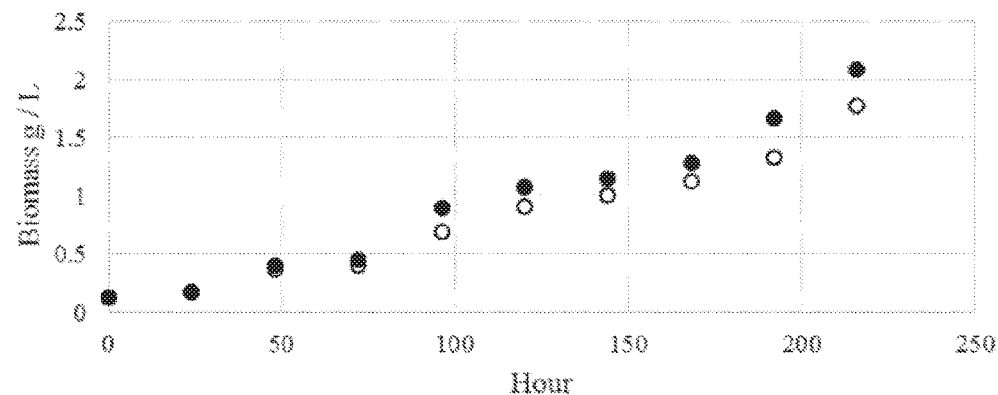

Two experimental factors are believed to be responsible for the foregoing deviations from the predicted trends. First, certain amounts of algae cells settled and adhered onto the surfaces of the zig-zag scaffolds of the Accordion air-loop bioreactors. While the scaffolds were gently moved up and down within the bioreactor to displace as much of the algae cells from the scaffold surfaces before liquid culture samples were collected for biomass concentration measurements, quantities of algae cells remained adhered to the scaffold surfaces notwithstanding. This had the effect of underestimating or undervaluing the algae concentrations in the Accordion air-loop treatments, explaining their significantly lower reported algae biomass concentrations. A separate experiment was conducted wherein the algae biomass concentrations in the Accordion air-loop treatments and in the double airlift control were measured before and after adhering algae cells were gently removed from the scaffold surfaces by sloughing them off using a finger (FIGS. 19A-19C). The summarized results in Table 3 show that algae adherence to scaffold surfaces resulted in the undervaluation of the final algae biomass concentration by approximately 17% in the single air-loop Accordion and by approximately 36% in the double air-loop Accordion. The double airlift control had an undervaluation by approximately 13%.

TABLE 3

Final biomass for *Scenedesmus obliquus* in Air-loop and Airlift bioreactors at high gas flow rate (0.3 vvm) before and after adhering algae cells were gently removed from the scaffold surfaces

| | Final Cell Concentration (g/L) | |
| --- | --- | --- |
| Reactor | Before (with settled algae) | After (without settled algae) (% change) |
| Double Airloop Accordion | 1.01 | 1.38 (36%) |
| Double Airlift | 1.27 | 1.43 (13%) |
| Single Airloop Accordion | 1.78 | 2.09 (17%) |

Second, the single air-loop Accordion and the single airlift control, by virtue of their narrower thickness, were effectively exposed to higher light levels than were the double air-loop Accordion and the double airlift control. With the thickness of the single-scaffold bioreactors being half of that for the double-scaffold bioreactors, and with the light source being directly incident on one thickness side of all the bioreactors, the single-scaffold bioreactors were receiving significantly greater diffused light from both of their sides than were the double-scaffold bioreactors. By a rough approximation, the diffused light from the sides reaching the center of a single-scaffold bioreactor was 400 percent of that reaching the center of a double-scaffold bioreactor. This had the effect of overestimating or overvaluing the algae concentrations in the single-scaffold bioreactors relative to the double-scaffold bioreactors, accounting in part for the significantly higher reported algae biomass concentrations in the single-scaffold bioreactors.

Thus, at high gas flow rate (0.3 vvm), by accounting for correction factors based on the unexpected algae cell adherence on the scaffold surfaces of the Accordion air-loop bioreactors and based on the single-scaffold bioreactors having received significantly higher diffused light than did the double-scaffold bioreactors, the adjusted results were in agreement with the predicted results, that is, that at high gas flow rate the two air-loop Accordion treatments and the two airlift controls should all have comparable algae biomass growths given the closeness of their high kla values and of their predominantly medium mixing time values. At low gas flow rate (0.1 vvm), by also accounting for similar correction factors as in the case of the high gas flow rate, the adjusted results were in agreement with the predicted results, that is, that at low gas flow rate the two air-loop Accordion treatments and the two airlift controls should all have comparable algae biomass growths given the closeness of their low kla values and of their slow and medium mixing time values.

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

We claim:

1. A bioreactor comprising:
   (a) a vessel comprising sides and a bottom;
   (b) at least one opening in the vessel connected to a means for introducing a gas; and
   (c) at least one scaffold inside the vessel and oriented substantially vertically in the vessel, wherein the at least one scaffold comprises a first sheet and a second sheet, wherein the first sheet and the second sheet are substantially parallel, and wherein two or more portions of the first sheet and the second sheet are oriented at alternating angles different than 0° relative to the horizontal axis of the vessel, and wherein the angle different than 0° is about 30° to 50°.

2. The bioreactor of claim 1, wherein the angle different than 0° relative to the horizontal axis of the vessel is about 30° or about 45°.

3. The bioreactor of claim 1, wherein the two or more portions of the first sheet and the second sheet oriented at an angle different than 0° relative to the horizontal axis of the vessel are curved.

4. The bioreactor of claim 1, wherein the at least one opening in the vessel connected to the means for introducing a gas is an opening in a side of the vessel.

5. The bioreactor of claim 1, wherein the means for introducing a gas comprises a gas sparger or a carbon dioxide diffuser.

6. The bioreactor of claim 1, wherein the scaffold comprises a rigid material selected from polycarbonate, polyvinyl chloride, glass, and stainless steel.

7. A method of culturing cells, comprising incubating a suspension of cells in a nutrient solution in the bioreactor of claim 1, and providing mixing by introducing a gas through the at least one opening in the vessel.

8. The method of claim 7, wherein the headspace between the top of the scaffold and the level of the nutrient solution is at least 0.5 inches.

9. The method of claim 7, wherein introducing the gas comprises a gas flow rate of about 0.05 to 0.5 volume per volume per minute.

10. The method of claim 7, wherein the cells comprise microalgal cells, macroalgal cells, bacterial cells, fungal cells, insect cells, plant cells, or mammalian cells.

11. The method of claim 7, wherein the bioreactor is exposed to a light source.

12. A bioreactor comprising:
    (a) a vessel comprising sides and a bottom;
    (b) at least one opening in the vessel connected to a means for introducing a gas; and
    (c) at least two scaffolds inside the vessel and oriented substantially vertically in the vessel, wherein each of the at least two scaffolds comprises a first sheet and a second sheet, wherein the first sheet and the second sheet are substantially parallel, and wherein two or more portions of the first sheet and the second sheet of each of the at least two scaffolds are oriented at alternating angles different than 0° relative to the horizontal axis of the vessel, and wherein the angle different than 0° is about 30° to 50°.

13. The bioreactor of claim 12, wherein the angle different than 0° relative to the horizontal axis of the vessel is about 30° or about 45°.

14. The bioreactor of claim 12, wherein the two or more portions of the first sheet and the second sheet of each of the at least two scaffolds oriented at an angle different than 0° relative to the horizontal axis of the vessel are curved.

15. The bioreactor of claim 12, wherein the at least one opening in the vessel connected to the means for introducing a gas is an opening in a side of the vessel.

16. The bioreactor of claim 12, wherein the means for introducing a gas comprises a gas sparger or a carbon dioxide diffuser.

* * * * *